United States Patent [19]

Janusz

[11] Patent Number: 4,692,512
[45] Date of Patent: Sep. 8, 1987

[54] ALPHA-L-ASPARTYL-D-PHENYLGLYCINE ESTERS AND AMIDES USEFUL AS HIGH INTENSITY SWEETENERS

[75] Inventor: John M. Janusz, Fairfield, Ohio

[73] Assignee: The Procter & Gamble Company, Cincinnati, Ohio

[21] Appl. No.: 811,585

[22] Filed: Dec. 20, 1985

Related U.S. Application Data

[63] Continuation-in-part of Ser. No. 630,504, Jul. 13, 1984, abandoned.

[51] Int. Cl.$^4$ ............................................. A23L 1/236
[52] U.S. Cl. ........................................ 530/801; 560/39; 560/41; 562/427; 562/430; 562/444; 562/450
[58] Field of Search ...................... 260/998.21; 560/39, 560/41; 562/444, 450, 427, 430; 530/801

[56] References Cited

U.S. PATENT DOCUMENTS

| | | | |
|---|---|---|---|
| 3,492,131 | 1/1970 | Schlatter | 426/548 |
| 3,714,139 | 1/1973 | Schlatter | 426/548 |
| 3,795,746 | 3/1974 | Walton | 426/548 |
| 3,801,563 | 4/1974 | Nakajima et al. | 260/998.2 |
| 3,853,835 | 12/1974 | Mazur et al. | 426/548 |
| 3,907,766 | 9/1975 | Fujino et al. | 426/217 |
| 3,920,626 | 11/1975 | Ariyoshi et al. | 426/548 |
| 3,971,822 | 7/1976 | Chibata et al. | 260/998.2 |
| 3,972,860 | 3/1976 | Moriarty et al. | 426/548 |
| 3,978,034 | 8/1976 | Sheehan et al. | 426/548 |
| 4,029,701 | 6/1977 | Haas et al. | 426/548 |
| 4,031,258 | 6/1977 | Haas et al. | 426/548 |
| 4,153,737 | 5/1979 | Berg et al. | 426/548 |
| 4,183,909 | 1/1980 | Schon et al. | 426/548 |
| 4,353,922 | 10/1982 | Pfister | 546/272 |
| 4,399,163 | 3/1983 | Brennan et al. | 426/548 |
| 4,411,925 | 10/1983 | Brennan et al. | 426/548 |
| 4,439,460 | 3/1984 | Tsau et al. | 426/548 |
| 4,448,716 | 5/1984 | Tsau | 426/271 |
| 4,571,345 | 2/1986 | Verlander et al. | 562/561 |

FOREIGN PATENT DOCUMENTS

| | | |
|---|---|---|
| 48051 | 3/1982 | European Pat. Off. . |
| 95772 | 12/1983 | European Pat. Off. . |
| 58-175470 | 10/1983 | Japan . |
| 411301 | 3/1976 | Spain . |

OTHER PUBLICATIONS

Kirk-Othmer, Encyclopedia of Chemical Technology, (1983), p. 448.
Goodman et al., "Peptide Sweeteners: A Model for Peptide and Taste Receptor Interactions," Proc. 15th Eur. Pop. Symp., (1974), pp. 271-278.
Goodman et al., "Peptide Based Sweetening Agents," FD 00590-04, FY 76.
Sukehiro et al., "Studies in Structure-Taste Relationships of Aspartyl Peptide Sweeteners: Syntheses and Properties of L-Aspartyl-D-Alanine Amides," Science of Human Life, vol. 11, (1977), pp. 9-16.
Fujino et al., "Structure-Taste Relationships of L-Aspartyl-Aminomalonic Acid Diesters," Chem. Pharm. Bull., vol. 24, (1976), pp. 2112-2117.
Mazur et al., "Synthetic Sweeteners: Aspartyl Dipeptide Esters from L- and D-Alkylglycines," J. Med. Chem., vol. 16, (1973), pp. 1284-1286.
Ariyoshi, "The Structure-Taste Relationships of Aspartyl Dipeptide Esters and beta-Hydroxy Amino Acids," Bull. Chem. Soc. Jap., vol. 47 (1974), pp. 326-330.
Ariyoshi, "The Structure-Taste Relationships of Aspartyl Dipeptide Esters," Agr. Biol. Chem., vol. 40, (1976), pp. 983-992.
Miyoshi, et al., "Structure-Taste Relationship of Novel alpha-L-Aspartyl Dipeptide Sweeteners," Bull. Chem. Soc. Jap., vol. 51, (1978), pp. 1433-1440.
Yamada et al., "A New Type of Olefinic Cyclization of Geraniol with Thallium (III) Perchlorate," J. Chem. Soc. Chem. Comm., (1976), pp. 997-998.
Nace, Organic Reactions, vol. 12, (1966), pp. 57-90.
Meinwald et al., "Highly Strained Bicyclic System: The Synthesis of Optically Active 2 alpha- and 2 beta-Amino and Hydroxy Bicyclo [2,1,1] Hexanes," J. Amer. Chem. Soc., vol. 82, (1960), pp. 5445-5450.
Brown et al., "Selective Reductions: The Stereochemistry of Reduction of Cyclic and Bicyclic Ketones by the Alkoxy-Substituted Lithium Aluminum Hydrides," J. Am. Chem. Soc., vol. 87, (1965), pp. 5620-5625.
Tabushi et al., "Sulfur-Carbonyl Interaction in Rigid beta-Keto Sulfides, Bull. Chem. Soc. Jap., vol. 51, (1978), pp. 1178-1182.
Tabushi et al., "Solvolyses of 2-endo- and 2-exo--Chloro-7-thiabicyclo(2.2.1) Heptanes," J. Am. Chem. Soc., vol. 97, (1975), pp. 2886-2891.
Tabushi et al., "The Extrusion Reaction of Sulfur Dioxide from Strained Sulfolene," Tet. Lett., No. 44, (1976), pp. 3957-3960.
Mariano et al., "Photochemistry of N-Allyliminium Salts: A Novel Photocyclization Reaction Leading to Pyrrolidines," J. Am. Chem. Soc., vol. 99, (1977), pp. 6781-6782.
Kaiser et al., "Natural Occurrence of New Ionone Derivatives and Their Structural Assignments by Synthetic Approaches," Int'l Congr. Essent. Oils 7th, vol. 7, (1979), pp. 395-399.

Primary Examiner—John Kight
Assistant Examiner—Nathan M. Nutter
Attorney, Agent, or Firm—Eric W. Guttag; David K. Dabbiere; Steven J. Goldstein

[57] ABSTRACT alpha-L-Aspartyl-D-phenylglycine esters and amides are disclosed to be useful as high intensity sweeteners. These compounds can be used to sweeten a variety of foods, beverages and other oral products.

22 Claims, No Drawings

ALPHA-L-ASPARTYL-D-PHENYLGLYCINE ESTERS AND AMIDES USEFUL AS HIGH INTENSITY SWEETENERS

CROSS-REFERENCE TO RELATED APPLICATIONS

This application is a continuation-in-part of U.S. application Ser. No. 630,504, filed July 13, 1984 and now abandoned.

TECHNICAL FIELD

The present application relates to alpha-L-aspartyl-D-phenylglycine and alpha-L-aspartyl-D-heteroaromatic-substituted glycine esters and amides useful as high intensity sweeteners.

Sweeteners are used in a variety of orally ingested products. For example, sweeteners are an important component of cakes, cookies, chewing gum, dentifrices and the like. Sweeteners are a particularly important ingredient in beverages. In terms of volume, carbonated beverages use more sweeteners than any other sweetened product category.

The most widely used sweetener for food, and especially beverage products, is sucrose. Sucrose is safe, naturally occurring, and has a high sweetness quality in terms of a pure, quick onset of sweetness with no aftertaste or undertaste. However, the normal usage of sucrose provides significant caloric load which is undesirable for those persons on weight control or reduction programs. Also, those persons who have diabetes must carefully control their intake of sucrose to avoid problems associated with the disease. Sucrose is also cariogenic so that it cannot be used in dentifrices and is undesirable in chewing gums. Additionally, and perhaps little realized, for the amount of sweetness delivered, sucrose can be expensive relative to other sweeteners such as saccharin, especially when used in carbonated beverages.

The drawbacks of sucrose, including its expense, have led those in the beverage industry to seek substitute sweeteners. One particularly important quality sought in such sweeteners is high sweetness intensity. Sweetness intensity can affect not only the safety profile and caloric value of the sweetener, but also its cost in terms of sucrose equivalent sweetness. However, the inability to predict that a given compound is sweet, and particularly that it has high sweetness intensity, makes the search for suitable substitute sweeteners a "hit-or-miss" proposition.

Such unpredictability is especially true for the L-aspartic acid derived sweeteners represented by the following formula:

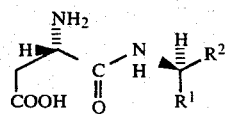

Various theories have been proposed for what imparts sweetness to these particular molecules. However, the current belief is that groups $R^1$ and $R^2$ need to be dissimilar in size for greatest sweetness intensity, i.e. one group large or bulky, the other group small. See Goodman et al., "Peptide Sweeteners: A Model for Peptide and Taste Receptor Interactions," *Proc. 15th Eur. Pep. Symp.*, (1974), pp. 271–78; Sukehiro et al., "Studies on Structure-Taste Relationships of Aspartyl Peptide Sweeteners: Syntheses and Properties of L-Aspartyl-D-Alanine Amides," *Science of Human Life*, Vol. 11, (1977), pp. 9–16. In addition, for the molecule to be sweet, the absolute stereochemistry must be as shown in the above formula with $R^1$ the small group and $R^2$ the large or bulky group. Generally, the smaller the $R^1$ group is, the higher the sweetness intensity of the molecule. See U.S. Pat. No. 3,972,860 to Moriarty et al., issued Aug. 3, 1976 (L-aspartyl-L-phenylglycine alkyl esters are sweet) where $R^1$ is a small alkyl ester group and $R^2$ is a phenyl group; U.S. Pat. No. 3,492,131 to Schlatter, issued Jan. 27, 1970 (L-aspartyl-L-phenylalanine alkyl esters are sweet) where $R^1$ is a small alkyl ester group and $R^2$ is a benzyl group. See also U.S. Pat. No. 4,411,925 to Brennan et al., issued Oct. 25, 1983 (L-aspartyl-D-alanine amides are sweet) where $R^1$ is a methyl group and $R^2$ is a branched alkyl, cycloalkyl or bicycloalkyl amide group; Ariyoshi et al., "The Structure-Taste Relationships of the Dipeptide Esters Composed of L-Aspartic Acid and Beta-Hydroxyamino Acids," *Bull. Chem. Soc. Jap.*, Vol. 47, (1974), pp. 326–30 (L-aspartyl-D-serine esters are sweet) where $R^1$ is a hydroxymethyl group and $R^2$ is a $C_1$–$C_4$ alkyl or cyclohexyl ester group. Even with these guidelines, the sweetness intensity of these L-aspartic acid derived sweeteners can vary greatly depending upon which combination of $R^1$ and $R^2$ groups are selected. Compare U.S. Pat. No. 4,411,925, supra ($R^1$ is a methyl group and $R^2$ is 2,6-dimethylcyclohexyl amide group, sweetness intensity is 600 times that of sucrose), with U.S. Pat. No. 3,907,766 to Fujino et al., issued Sept. 23, 1975 ($R^1$ is a methyl ester group and $R^2$ is a fenchyl ester group, sweetness intensity is 22,200–33,200 times that of sucrose).

For beverage use, the substitute sweetener must be sufficiently soluble and hydrolytically stable. Most carbonated beverages have a pH of from about 2.5 to about 4.8. Useful sweeteners in such beverages must therefore be relatively resistant to acid catalyzed breakdown. Otherwise, the beverage can quickly lose its sweetness or possibly have undesirable off-flavors imparted to it. As in the case of sweetness intensity, it can be difficult to predict whether a given sweetener will be hydrolytically stable, especially in an acidic environment.

Other factors are also important in providing a useful substitute sweetener. To obtain approval for food or beverage use, the substitute sweetener must be safe in terms of acute toxicity as well as long-term effects from continued use. The substitute sweetener should also desirably approach sucrose in terms of sweetness quality, as well as have a relatively quick onset and short duration of sweetness. Finally, to be classified as a non-caloric sweetener, the substitute sweetener (or metabolic products thereof) should provide minimal or no caloric value at normal usage levels.

A widely used substitute sweetener is saccharin, in particular its sodium salt. Saccharin has a relatively high sweetness intensity (about 300 times that of sucrose) and is relatively inexpensive in providing sucrose equivalent sweetness in carbonated beverages. However, saccharin also provides an undesirable lingering bitter aftertaste.

Besides saccharin, a number of the L-aspartic acid derived amides have been proposed as suitable substitute sweeteners. The most prominent example is the alpha-L-aspartyl-L-phenylalanine methyl ester known as aspartame. Aspartame has been approved for use in dry foods and beverages, including carbonated beverages. The sweetness intensity of aspartame is about 150-200 times that of sucrose with a sweetness quality approaching that of sucrose. The caloric value of aspartame is also relatively minimal at normal usage levels. However, aspartame is hydrolytically unstable in most carbonated beverages. Perhaps more important to the beverage industry, aspartame is extremely expensive in terms of sucrose equivalent sweetness delivered.

The search therefore continues for substitute sweeteners which are: (1) inexpensive in terms of sucrose equivalent sweetness; (2) are hydrolytically stable in carbonated beverage systems; (3) are safe; (4) have satisfactory taste quality; and (5) provide minimal caloric value.

BACKGROUND ART

A. L-aspartyl-L-phenylglycine esters

U.S. Pat. No. 3,972,860 to Moriarty et al., issued Aug. 3, 1976, discloses L-aspartyl-L-phenylglycine lower alkyl ester sweeteners. The preferred methyl ester is disclosed as having a sweetness intensity of from 100-1000 times that of sucrose. See also Goodman et al., "Peptide Sweeteners: A Model for Peptide and Taste Receptor Interactions," *Proc. 15th Eur. Pep. Symp.*, (1974), pp. 271-78, which discloses that the methyl ester of L-aspartyl-L-phenylglycine is "quite sweet."

B. Peptides Containing D-phenylglycine

U.S. Pat. No. 4,183,909 to Schon et al. issued Jan. 15, 1980, discloses phenylglycine-containing peptides which greatly increase gastric acid secretion when administered intravenously. One of the precursors of these peptides is the beta-tert-butyl ester of L-aspartyl-D-phenylglycine hydrochloride (Example 1, Step 4).

C. L-aspartyl-D-alanine amides

U.S. Pat. No. 4,411,925 to Brennan et al. issued Oct. 23, 1983, discloses L-apartyl-D-alanine amide sweeteners. These amides have the formula:

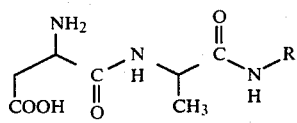

wherein R is a branched hydrocarbyl group, including fenchyl (320 times as sweet as sucrose). The highest intensity sweeteners include those where R is 2,5 dimethylcyclopentyl (520 times that of sucrose), 2,6-dimethylcyclohexyl (600 times that of sucrose), dicyclopropylcarbinyl (1200 times that of sucrose) 2,2,4,4-tetramethylthietan-3-yl (2000 times that of sucrose), or 2,2,4,4-tetramethyl-1,1-dioxothietan-3-yl (1000 times that of sucrose). See also Sukehiro et al., "Studies on Structure-Taste Relationships of Aspartyl Peptide Sweeteners: Syntheses and Properties of L-Aspartyl-D-Alanine Amides," *Science of Human Life*, Vol. 11, (1977), pp. 9-16, which discloses L-aspartyl-D-alanine amide sweeteners (10 to 125 times that of sucrose) wherein R is $C_2$-$C_4$ alkyl or cyclohexyl.

D. L-aspartyl-aminomalonic acid diesters

U.S. Pat. No. 3,907,766 to Fujino et al., (assigned to Takeda Chemical Industries, Ltd.), issued Sept. 23, 1975 discloses L-aspartyl-aminomalonic diester sweeteners. These diesters have the formula:

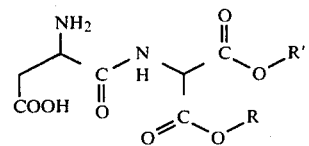

wherein R' is fenchyl and R is methyl (22,200-33,200 times that of sucrose) or ethyl (4200-5400 times that of sucrose). Fujino et al., "Structure-Taste Relationships of L-aspartyl-aminomalonic Acid Diesters, " *Chem. Pharm. Bull.*, Vol. 24 (1976), pp. 2112-17, suggests that the L-aspartyl-L-aminomalonic acid diester is the sweet one. See page 2116. See also U.S. Pat. No. 3,801,563 to Nakajima et al. (assigned to Takeda Chemical Industries, Ltd.), issued Apr. 2, 1974, which discloses other L-aspartyl-aminomalonic acid diesters containing branched or cyclic alkyl ester groups.

E. L-aspartyl-D-amino acid esters

Mazur et al., "Synthetic Sweeteners:Aspartyl Dipeptide Esters from L- and D-alkylglycines,"*J. Med. Chem.*, Vol. 16, (1973), pp. 1284-87, discloses sweetness intensity testing of isopropyl esters of L-aspartyl-D-amino acids. These esters have the formula:

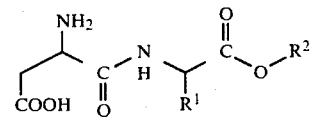

wherein $R^2$ is isopropyl and $R^1$ is a $C_1$-$C_4$ alkyl group. The sweetness of intensity of the particular esters ranges from 0-170 times that of sucrose.

Ariyoshi et al., "The Structure-Taste Relationships of the Dipeptide Esters Composed of L-aspartic Acid and Beta-hydroxyamino Acids," *Bull. Chem. Soc. Jap.*, Vol. 47, (1974), pp. 326-30, discloses sweetness intensity testing of $C_1$-$C_4$ alkyl or cyclohexyl esters of L-aspartyl-D-amino acids. These esters have the formula:

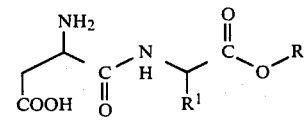

wherein $R^2$ is a $C_1$-$C_4$ alkyl or cyclohexyl group, and $R^1$ is a $C_1$-$C_2$ alkyl or hydroxyalkyl group. The D-amino acids used include D-serine ($R^1$=hydroxymethyl); D-threonine ($R^1$=hydroxyethyl), D-allo-threonine ($R^1$=a-hydroxyethyl), and D-2-aminobutyric acid ($R^1$=ethyl). The sweetness intensity of the particular esters can range from 6-320 times that of sucrose.

Ariyoshi "The Structure-Taste Relationships of Aspartyl Dipeptide Esters," *Agr. Biol. Chem.*, Vol. 40, (1976), pp. 983-92, discloses sweetness intensity testing of $C_1$-$C_3$ alkyl or cyclohexyl esters of L-aspartyl-D-amino acids. These esters have the formula:

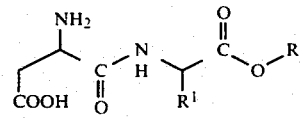

wherein R is a $C_1$-$C_3$ alkyl or cyclohexyl group, and $R^1$ is a $C_1$-$C_3$ alkyl or hydroxyalkyl, or benzyl group. The methyl ester of L-aspartyl-D-phenylalanine is disclosed to be bitter.

See also U.S. Pat. No. 3,492,131 to Schlatter (assigned to G. D. Searle & Co.), issued Jan. 27, 1970, which states that the L-aspartyl-D-phenylalanine esters are not sweet.

DISCLOSURE OF THE INVENTION

The present invention relates to certain alpha-L-aspartyl-D-phenylglycine and alpha-L-aspartyl-D-heteroaromatic-substituted glycine esters and amides useful as sweeteners. These esters and amides include the non-toxic salts and have the formula:

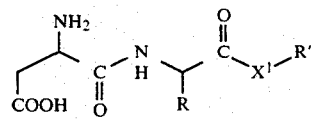

wherein the ester or amide is the L,D stereochemical isomer; wherein $X^1$ is O or NH; wherein R is a phenyl group having the formula:

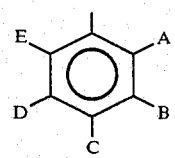

wherein A, B, C, D and E are H, OH, F, Cl, Br, or $C_1$-$C_4$ alkyl, hydroxyalkyl or alkoxy or wherein R is a heteroaromatic group having a 5 or 6 member heteroaromatic ring selected from the group consisting of furyl, thienyl, pyrryl, oxazolyl, thiazolyl, imidazolyl, isoxazolyl, isothiazolyl, pyrazolyl, oxadiazolyl, thiadiazolyl, triazolyl, tetrazolyl, pyridyl, pyrazinyl, pyrimidinyl, pyridazinyl and triazinyl; and wherein R' is selected from the group consisting of hydrocarbyl radicals having formulas (a) (b) (c) (d) (e) (f) and (g):

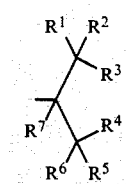
(a)

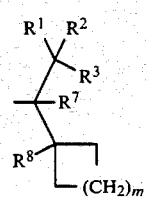
(b)

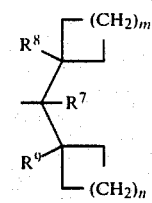
(c)

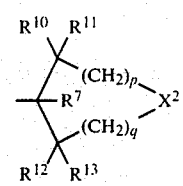
(d)

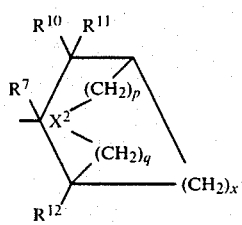
(e)

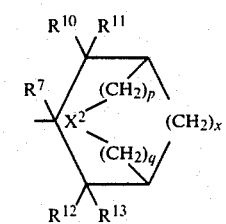
(f)

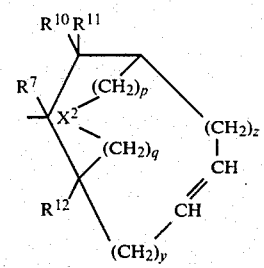
(g)

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are H, or $C_1$-$C_4$ alkyl, hydroxyalkyl or alkoxy; $X^2$ is $CH_2$, O, S, SO, $SO_2$, C=O, $CR^{14}OH$, $NR^{14}$

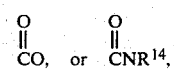

wherein $R^{14}$ is H or $C_1$-$C_2$ alkyl or hydroxyalkyl; provided that when R is a hydrocarbyl radical of formula (e), (f) or (g), $R^{10}$, $R^{11}$, $R^{12}$ and $R^{13}$ are each H when $X^2$ is other than $CH_2$ or O; m is 0, 1, 2, 3 or 4; N is 0, 1, 2, 3 or 4; p and q are 0, 1, 2 or 3 and the sum of p+q is not greater than 3; x is 1, 2 or 3; y and z are 0, 1 or 2 and the sum of y+z is not greater than 2.

These alpha-L-aspartyl-D-phenylglycine and alpha-L-aspartyl-D-heteroaromatic-substituted glycine esters and amides are more hydrolytically stable in carbonated beverages than aspartame. Also, certain of these esters and amides have sufficiently high sweetness intensity so as to be relatively inexpensive in terms of sucrose equivalent sweetness. Based on available data for the expected metabolites, it is believed that these esters and amides are safe for use in food and beverage systems, and will provide minimal caloric value at normal usage levels. The taste quality of these sweeteners is satisfactory. The onset and duration of sweetness for some of these esters or amides can be somewhat slower and more lingering than that of sucrose. Accordingly, mixtures of these esters or amides with other sweeteners having a quicker onset of sweetness are sometimes preferred.

A. Alpha-L-aspartyl-D-phenylglycine and alpha-L-aspartyl-D-heteroaromatic-substitued glycine esters and amides The esters and amides of the present invention have the formula:

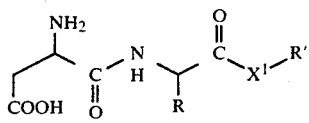

It has been determined (or for the alpha-L-aspartyl-D-heteroaromatic-substituted glycines, it is believed based on the absolute stereochemistry required for sweetness) that the L, D stereochemical isomer imparts the sweetness character to these esters and amides. However, minor amounts of the D,L, L, L and D, D stereochemical isomers can be tolerated without adversely affecting the taste quality of L,D stereochemical isomer. Such diastereomeric mixtures typically comprise at least about 50% of the L,D stereochemical isomer, preferably at least about 70% of the L,D isomer, and most preferably at least about 95% of the L,D isomer.

The esters or amides of the present invention can be in the form of non-toxic salts. As used herein, "non-toxic salts" means salts of the present esters and amides which are physiologically acceptable for ingestion. Such salts include both cationic and acid addition salts of these esters and amides. By "cationic salts" is meant those salts formed by neutralization of the instant esters and amides by bases of physiologically acceptable metals, ammonia and amines. Examples of such metals are sodium, potassium, calcium and magnesium. Examples of such amines are N-methyl-glucamine and ethanolamine. By "acid addition salts" is meant those salts formed between the instant esters and amides and a physiologically acceptable acid. Examples of such acids are acetic, benzoic, hydrobromic, hydrochloric, citric, fumaric, gluconic, lactic, maleic, malic, sulfuric, sulfonic, nitric, phosphoric, saacharic, succinic and tartaric acids.

The compounds of the present invention can be in the form of either esters or amides ($X^1$ is O or NH). The esters and amides have acceptable hydrolytic stability and in particular have a hydrolytic stability greater than that of aspartame. In terms of sweetness intensity, the esters tend to have a greater sweetness intensity.

The phenyl group R of the esters or amides of the present invention has the formula:

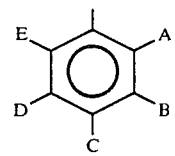

wherein A, B, C, D and E are H, OH, F, Cl, Br or $C_1-C_4$ alkyl, hydroxyalkyl or alkoxy. Preferred groups R are those where A, B, C, D and E are all H or where one of A, B, C, D and E is OH or F. Particularly preferred groups R are phenyl (A, B, C, D and E are each H), p-hydroxyphenyl (C is OH; A, B, D and E are H), and o-fluorophenyl. (A is F; B, C, D and E are H).

The heteroaromatic group R of the esters or amides of the present invention have a 5 or 6 member heteroaromatic ring selected from furyl, thienyl, pyrryl, oxazolyl, thiazolyl, imidazolyl, isoxazolyl, isothiazolyl, pyrazolyl, oxadiazolyl, thiadiazolyl, triazolyl, tetrazolyl, pyridyl, pyrazinyl, pyrimidinyl, pyridazinyl and triazinyl. The heteroaromatic ring can be substituted or unsubstituted. The substituents on substituted rings are selected so as not to substantially decrease the sweetness intensity of the esters and amides of the present invention. Suitable substituents include $C_1-C_4$ alkyl (methyl, ethyl, propyl, butyl) and alkoxy (methoxy, ethoxy, propoxy, butoxy) groups. Preferably, the heteroaromatic ring is unsubstituted for the esters and amides of the present invention.

Suitable heteroaromatic groups R for the esters and amides of the present invention include 2-furyl, 3-furyl, 2-thienyl, 3-thienyl, 2-pyrryl, 3-pyrryl, 2-oxazolyl, 4oxazolyl, 5-oxazoyl, 2-thiazolyl, 4-thiazolyl, 5-thiazoyl, 2-imidazolyl, 4-imidazolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,3,4-thiadiazol-2-yl, 1,2,3-triazol-4-yl, 1,2,4-triazol-3-yl, tetrazolyl, 2-pyridyl, 3-pyridyl, 4-pyridyl, pyrazinyl, 2-pyrimidinyl, 4-pyrimidinyl, 5-pyrimidinyl, 3-pyridazinyl, 4-pyridazinyl, 1,2,3-triazin-4-yl, 1,2,3-triazin-5-yl, 1,2,4-triazin-3-yl, 1,2,4-triazin-5-yl, 1,2,4-triazin-6-yl and 1,3,5-triazin-2-yl. Preferred heteroaromatic groups are 2-furyl, 2-thienyl and 3-thienyl.

The terminal group R' can be selected from a variety of hydrocarbyl radicals. The first group of such radicals have the formula (a):

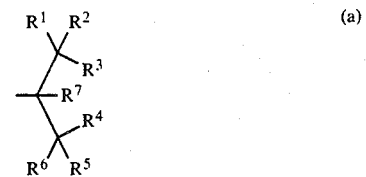

wherein $R^1$, $R^2$, $R^3$, $R^4$, $R^5$, $R^6$ and $R^7$ are H or $C_1-C_4$ alkyl, hydroxyalkyl or alkoxy. Preferably, $R^1$, $R^2$, $R^3$, $R^4$, $R^5$ and $R^6$ are selected from methyl or H; $R^7$ is preferably H. Particularly preferred radicals of formula (a) are diisopropylcarbinyl ($R^1$, $R^2$, $R^4$, $R^5$ are methyl; $R^3$, $R^6$ and $R^7$ are H); and especially 3,3-dimethyl-2- butyl ($R^1$, $R^2$, $R^3$ are methyl; $R^4$, $R^5$, $R^6$ and $R^7$ are hydrogen).

A second group of such radicals have the formula (b):

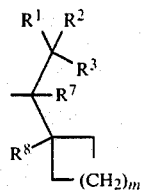

wherein $R^1$, $R^2$, $R^3$ and $R^7$ are defined as before; $R^8$ is H, or $C_1-C_4$ alkyl, hydroxyalkyl or alkoxy; and m is 0, 1, 2, 3 or 4. A particularly preferred radical of formula (b) is tert-butyl cyclopropylcarbinyl ($R^1$, $R^2$, $R^3$ are methyl; $R^7$ and $R^8$ are hydrogen; m is 0).

A third group of such radicals have the formula (c):

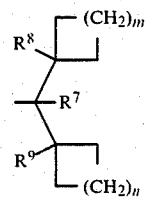

wherein m, $R^7$ and $R^8$ are defined as before; $R^9$ is H or $C_1-C_4$ alkyl, hydroxyalkyl or alkoxy; and n is 0, 1, 2, 3 or 4. A particularly preferred radical of formula (c) is dicyclopropylcarbinyl ($R^7$, $R^8$ and $R^9$ are each H; m and n are 0).

A fourth group of such radicals have the formula (d):

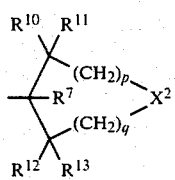

wherein $R^7$ is defined as before; $R^{10}$, $R^{11}$, $R^{12}$ and $R^{13}$ are H or $C_1-C_4$ alkyl, hydroxyalkyl or alkoxy; $X^2$ is $CH_2$, O, S, SO, $SO_2$, C=O, $CR^{14}OH$, $NR^{14}$,

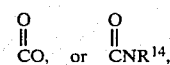

wherein $R^{14}$ is H or $C_1-C_2$ alkyl or hydroxyalkyl; p and q are each 0, 1, 2 or 3; the sum of p+q being not greater than 3. Preferably, $X^2$ is $CH_2$, S, SO or $SO_2$; $R^7$ and $R^{14}$ are preferably H. When $X^2$ is $CH_2$, at least one of $R^{10}$, $R^{11}$ and $R^{12}$ and $R^{13}$ is preferably methyl, ethyl, isopropyl or tert-butyl; the sum of p+q is preferably 1 or 2. Particularly preferred radicals of formula (d) when $X^2$ is $CH_2$ are 2-methylcyclohexyl; 2-ethylcyclohexyl; 2-isopropylcyclohexyl; 2-tert-butylcyclohexyl; 2,2-dimethylcyclohexyl; 2,6-dimethylcyclohexyl; 2,6-diethylcyclohexyl; 2,2,6-trimethylcyclohexyl; 2,2,6,6-tetramethylcyclohexyl; 2-isopropylcyclopentyl; 2-methylcyclopentyl; 2-ethylcyclopentyl; 2,2-dimethylcyclopentyl; 2,5-dimethylcyclopentyl, 2,2,5-trimethylcyclopentyl; 2,2,5,5-tetramethylcyclopentyl. Especially preferred are 2,5-dimethylcyclopentyl and 2,6-dimethylcyclohexyl. When $X^2$ is other than $CH_2$, $R^{10}$, $R^{11}$, $R^{12}$ and $R^{13}$ are preferably hydrogen or methyl; the sum of p+q is preferably 0, 1 or 2. Particularly preferred radicals of formula (d) when $X^2$ is other than $CH_2$ are 2,2,4,4-tetramethyltetrahydrofuran-3-yl; 2,2,4,4-tetramethylthietan-3-yl; 2,2,4,4-tetramethyl-1-oxothietan-3-yl; 2,2,4,4-tetramethyl-1,1-dioxothietan-3-yl; 2,2,4,4-tetramethyltetrahydrothiophene-3-yl; and 3,5-dimethyltetrahydrothiopyran-4-yl.

A fifth set of such radicals have the formula (e):

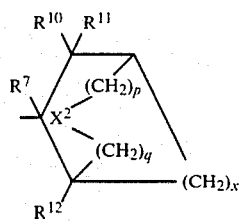

wherein $R^7$, $X^2$, p and q are defined as above; x is 1, 2 or 3; and $R^{10}$, $R^{11}$ and $R^{12}$ are H or $C_1-C_4$ alkyl, hydroxyalkyl or alkoxy when $X^2$ is $CH_2$ or O, and are H when $X^2$ is other than $CH_2$ or O. Preferably $R^{10}$, $R^{11}$ and $R^{12}$ are methyl or H; $R^7$ is preferably H; $X^2$ is preferably $CH_2$ or O; the sum of p+q is preferably 0; x is preferably 2. Examples of radicals of formula (e) are (±)-endo-norbornyl; (±)-exo-norbornyl; (±)-endo-7-oxanorbornyl ($X^2$ is O); (±)-exo-7-oxa-norbornyl ($X^2$ is O); (±)-alpha-fenchyl; (±) alpha-7-oxa-fenchyl ($X^2$ is O); (±)-beta-fenchyl; and (±) beta-7-oxa-fenchyl ($X^2$ is O). Especially preferred are (−)-alpha-fenchyl; (±)alpha-7-oxa-fenchyl; (+)-beta-fenchyl; and (±)-beta-7-oxa-fenchyl.

A sixth set of such radicals have the formula (f):

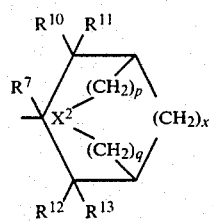

wherein $R^7$, $R^{10}$, $R^{11}$, $R^{12}$, $X^2$, p, q and x are defined as in formula (e); and $R^{13}$ is defined like $R^{10}$, $R^{11}$ or $R^{12}$. Preferably, $R^{10}$, $R^{11}$, $R^{12}$ and $R^{13}$ are methyl or H; $R^7$ is preferably H; $X^2$ is preferably $CH_2$ or O; the sum of p+q is preferably 0; x is preferably 2.

A seventh set of such radicals have the formula (g):

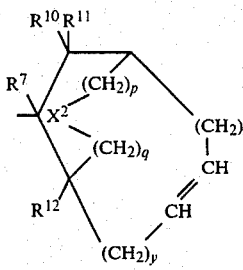

wherein $R^7$, $R^{10}$, $R^{11}$, $R^{12}$, $X^2$, p and q are defined as in formula (e); and y and z are 0, 1 or 2 and the sum of y+z is no greater than 2. Preferably, $R^{10}$, $R^{11}$ and $R^{12}$ are H or methyl; $R^7$ is preferably H; $X^2$ is preferably $CH_2$ or O; the sum of p+q is preferably 0; the sum of y+z is preferably 0 or 1.

B. Sweetness Intensity of Alpha-L-Aspartyl-D-Phenylglycine Esters and Amides

The sweetness intensity of the esters and amides of the present invention relative to sucrose was determined according to the following procedure:

Male subjects were chosen at random from a group of about 20 persons who had previously been selected on the basis of proven tasting acuity, i.e., persons who could easily recognize the four basic tastes (sweet, sour, bitter and salty) and who were adept at quantifying their own physiological response numerically. The subjects were asked to taste and expectorate about 10 ml of a test sample (temperature of about 22° C.) having dissolved therein the ester or amide. The subjects were then asked to compare the sweetness of the test sample with five standard samples which contained increasing amounts of sucrose. The standard samples were letter coded A, B, C, D and E and were designated on a ballot by a closed linear scale. Sweetness intensity of the test sample was recorded by the subject making a mark on the linear scale at a point he considered equal in sweetness among the standard samples; interpolation between standards was encouraged. After completion of the panel, a five point numeric scale was superimposed on the linear scales to obtain numerical data; data were averaged and recorded to the nearest 0.25 unit. Equivalent sucrose sweetness was determined by referring to graphs of (w/v) sucrose concentration in the standard samples versus a linear numeric scale.

Sweetness intensity was calculated by dividing the concentration (w/v) of perceived sweetness by the concentration (w/v) of the ester or amide required to produce that sweetness. The five point scale with standard samples ranging from 1.37% (0.040M) to 11.97% (0.35M) sucrose was used for sweetness intensity testing. The test sample was prepared at a concentration which would be equal to about 8–10% sucrose.

The sweetness intensity of the esters and amides of the present invention evaluated by this testing is presented in the following table:

| R Group | R' Group | $X^1$ Group | Sweetness (× Sucrose) |
|---|---|---|---|
| D-Phenyl | 3,3-dimethyl-2-butyl | O | 30 |
| D-Phenyl | 2,6-dimethylcyclohexyl | O | 210 |
| D-Phenyl | 2,5-dimethylcyclopentyl | O | 370 |
| D-Phenyl | (+)-alpha-fenchyl | O | 200 |
| D-Phenyl | (−)-alpha-fenchyl | O | 1750 |
| D-Phenyl | (±)-endo-norbornyl | O | 20 |
| D-Phenyl | (±)-exo-norbornyl | O | 150 |
| D-Phenyl | 2,2,5,5-tetramethyl-cyclopentyl | O | 400* |
| D-Phenyl | 2,2,4,4-tetramethyl-thietan-3-yl | 0 | 75–100* |
| D-Phenyl | (+)-beta-fenchyl | O | 5000* |
| D-Phenyl | (−)-beta-fenchyl | O | 600* |
| D-Phenyl | alpha-7-oxa-fenchyl | O | 1000* |
| D-Phenyl | dicyclopropylcarbinyl | NH | 80 |
| D-Phenyl | 2,2,4,4-tetramethyl-thietan-3-yl | NH | 100 |
| D-p-Hydroxyphenyl | (−)-alpha-fenchyl | O | 500* |
| D,L-o-Fluorophenyl | (−)-alpha-fenchyl | O | 1000* |
| D,L-2-furyl** | (+)-alpha-fenchyl | O | 600 |
| D-2-furyl | (+)-beta-fenchyl | O | 16,450 |
| D-2-furyl | 2,5-dimethylcyclopentyl | O | 500+* |
| D-2-thienyl | (+)-beta-fenchyl | O | 2,000* |
| D-3-thienyl | (+)-beta-fenchyl | O | 2,000* |
| D-2-furyl | 2,2,4,4-tetramethyl-thietan-3-yl | NH | 400* |
| D-2-furyl | (−)-alpha-fenchyl | NH | 200* |
| D-2-furyl | dicyclopropylcarbinyl | NH | 600* |

*Based on informal panel testing
**50:50 mixture of D-furyl:L-furyl isomers

C. Synthesis of alpha-L-aspartyl-D-phenylglycine and alpha-L-aspartyl-D-heteroaromatic-substituted glycine esters and amides The alpha-L-aspartyl-D-phenylglycine esters of the present invention can be synthesized according to the following 4-step reaction scheme:

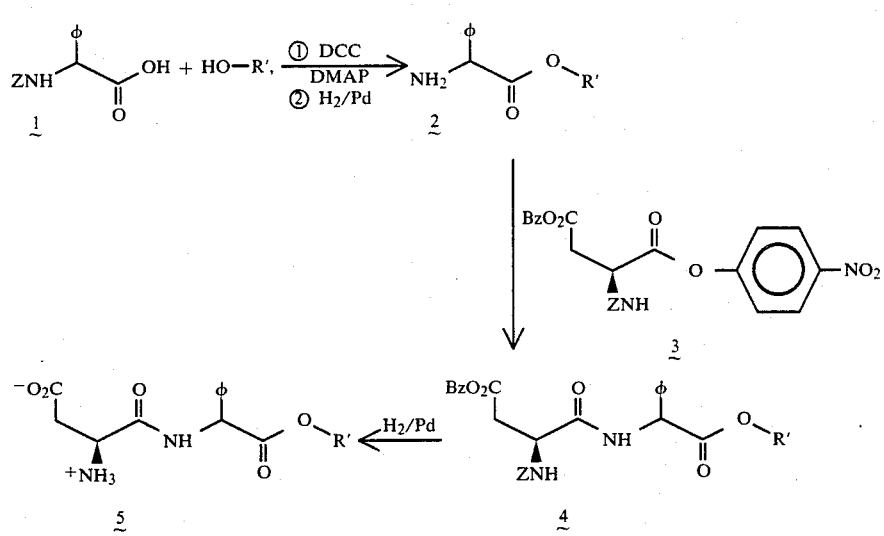

In the first step, carbobenzyloxy (Z) protected D-phenylglycine 1 is coupled with alcohol R'OH using dicyclohexylcarbodiimide (DCC)/dimethylaminopyridine (DMAP). In the second step, the ester formed in step 1 is hydrogenated over palladium to remove the protecting group to form the phenylglycine ester 2. In the third step, ester 2 is coupled to the protected activated L-aspartic ester 3 to form the protected L-aspartyl-D-phenylglycine ester 4. In the fourth step, the protecting groups are removed by hydrogenation of ester 4 over palladium to yield sweetener 5. Alcohols R'OH used in this synthesis are commercially available, can be obtained by art recognized methods, see U.S. Pat. No. 4,411,925 to Brennan et al., issued Oct. 25, 1983, (herein incorporated by reference) especially column 12, line 55 to column 20, line 9, or can be obtained by methods disclosed in the present application.

Syntheses of specific alpha-L-aspartyl-D-phenylglycine esters according to this reaction scheme are as follows:

EXAMPLE 1

(−)-alpha-Fenchyl ester

Step 1: N-Carbobenzyloxy-D-phenylglycine-(−)-alpha-fenchyl ester a. N-Carbobenzyloxy-D-phenylglycine To D-phenylglycine (50 g., 0.33 moles, Aldrich) was added 82 ml. of 4N NaOH. The mixture was cooled to 0° C. and carbobenzyloxy chloride (51 ml., 0.36 moles) was added dropwise. Additional NaOH was added as needed to keep the reaction mixture basic. After stirring for 10 minutes, 200 ml. of $H_2O$ was added. After 10 more minutes, the solution was filtered. The clear filtrate was extracted twice with ether and was then adjusted to pH 3 with 5N HCl. The resulting precipitate was filtered, washed twice with $H_2O$ and then dried. The crude product was dissolved in ethyl acetate and then filtered. The filtrate was evaporated and the resulting solid crystallized from ethyl acetate/hexane. Yield: 35 g. $[\alpha]_D = -108.5°$ (c 1.0, methanol)

b. (−)-alpha-Fenchol (+)-Fenchone (15 g., 0.098 moles, $[\alpha]_D = +65.5°$, Fluka) in 200 ml. of ether was added dropwise to a stirred suspension of $LiAlH_4$ (3.8 g, 0.10 moles) in 300 ml. of ether at 0° C. After 2 hours, the reaction was carefully quenched by dropwise addition of 3.8 ml. of $H_2O$, 3.8 ml. of 15% NaOH and 12 ml. of $H_2O$. The resulting precipitate was filtered and washed well with ether. The ether was dried over $MgSO_4$ and evaporated. The crude product was distilled at aspirator pressure at from 90° to 96° C. to give the desired product. Yield: 14.0 g. $[\alpha]_D = -12.4°$ (c 3.2, ethanol).

c. N-Carbobenzyloxy-D-phenylglycine-(−)-alpha-fenchyl ester

The N-carbobenzyloxy-D-phenylglycine (20 g., 0.07 moles) from step 1a was dissolved in about 150 ml. of dry methylene chloride. The (−)-alpha-fenchol (10.9 g., 0.07 moles) from step 1b and N,N'-dicyclohexylcarbodiimide (17.3 g., 0.083 moles) were then added after cooling the solution to 0° C. The mixture thickened; additional methylene chloride (about 150 ml.) was added. When the mixture became more uniform, it was then chilled to −65° C. 4 Dimethylaminopyridine was then added and the mixture stirred at −60° to −65° C. for 1 hour. The cooling bath was then changed to carbon tetrachloride/dry ice to maintain the mixture at −23° C. for 3 hours. The precipitated N,N'-dicyclohexylurea was filtered off. The filtrate was successively washed with chilled $H_2O$, 0.1N HCl, 2% $NaHCO_3$, $H_2O$ and brine. The filtrate was dried over $MgSO_4$ and then evaporated. Yield: 28.85 g. Identity of the desired ester was confirmed by NMR and IR spectroscopy. $[\alpha]_D = -41.2°$ (c 2.8, methanol)

Step 2: D-Phenylglycine-(−)-alpha-fenchyl ester

To a Parr flask was added 5% palladium on charcoal (200 mg). The crude ester (28.8 g.) from step 1c in about 200 ml. of methanol was then added. The contents of the flask were hydrogenated for 5 hours. Additional 5% palladium on charcoal (200 mg.) plus 10% palladium on charcoal (100 mg.) was added to the flask and hydrogenation was continued overnight. The contents of the flask were then filtered and evaporated to yield 19.3 g. of crude product. This crude product was dissolved in 0.1N HCl and was extracted twice with ether to remove non-basic impurities. The aqueous layer was adjusted to pH 9–10 with NaOH and was then extracted 3 times with ether. The combined extracts were successively washed with $H_2O$ and brine, and then dried over $MgSO_4$. The dried extracts were filtered and then evaporated to give the desired ester. Yield: 12.1 g. Identity of the ester was confirmed by NMR and IR spectroscopy. $[\alpha]_D = -49.0°$ (c 2.6, methanol).

Step 3: beta-Benzyl-N-carbobenzyloxy-L-aspartyl-D-phenylglycine-(−)-alpha-fenchyl ester a. beta-Benzyl-N-carbobenzyloxy-L-aspartyl-p-nitrophenyl ester To a 1000 ml. 3-neck flask was added beta-benzyl-N-carbobenzyloxy-L-aspartic acid (50 g., 0.14 moles, Bachem Inc.) p-nitrophenol (23.5 g., 0.17 moles) and about 350 ml. of ethyl acetate. This mixture was stirred and then 4-dimethylaminopyridine (1.0 g.) and N,N'-dicyclohexylcarbodiimide (28.5 g., 0.14 moles) was added. The solution became warm; after 4 hours, the reaction was complete as measured by thin layer chromatography. The solution was the filtered to remove precipitated N,N'-dicyclohexylurea and then extracted 9 times with saturated $Na_2CO_3$ solution, then 2 times with saturated NaCl solution. The extracted solution was dried over $Na_2SO_4$ and then concentrated to yield 60.5 g. of crude ester. This concentrated solution was dissolved in hot ethanol and then seeded. The concentrated solution was allowed to fully crystallize at room temperature and was then cooled with ice. The crystals were filtered and then washed with cold ethanol. Yield: 49.0 g. Identity of the desired ester was confirmed by NMR. M.P. 75°–77° C. $[\alpha]_D = +11.4°$ (c 1.0, chloroform).

b. beta-Benzyl-N-carbobenzyloxy-L-aspartyl-D-phenylglycine(−)-alpha-fenchyl ester The p-nitrophenyl ester from step 3a (19.6 g., 0.041 moles) was dissolved in 100 ml. of dry tetrahydrofuran (THF) and was chilled to 0° C. The fenchyl ester from step 2 (11.8 g., 0.041 moles) was added and the reaction mixture was then stirred at 0° C. for 1 hour. The reaction mixture was stirred overnight at room temperature and then the THF was evaporated. The residue was partitioned between ethyl acetate and $H_2O$. The organic layer was successively washed with cold 10% $Na_2CO_3$, $H_2O$, and brine, and then dried over $MgSO_4$. The dried solution was filtered and then evaporated to give 27 g. of crude product. This crude product was purified by silica gel chromatography first with 2% acetone/chloroform solvent and then with 25% ethyl acetate/hexane solvent. Yield: 17 g. The purified ester was characterized by NMR. $[\alpha]_D = -35.4°$ (c 1.8, methanol).

Step 4: alpha-L-Aspartyl-D-phenylglycine-(−)-alpha-fencyl ester

The purified ester from step 3b (7 g., 0.011 moles) was dissolved in 150 ml. of methanol and was then hydrogenated over 5% palladium on charcoal (300 mg.) for 22 hours. A second portion of the purified ester from step 3b (3 g., 0.013 moles) was hydrogenated over 10% palladium on charcoal (300 mg.) for 5 hours. The catalyst was filtered off and the solvent evaporated for a combined yield of 10.5 g. of the desired sweetener. The sweetener was characterized by NMR, IR and mass spectroscopy. M.P. 156°–158° C. $[\alpha]_D = -48.5°$ (C 1.0, methanol). HPLC analysis showed that this sweetener was approximately a 3:1 mixture of diastereomers. Sweetness intensity: 1750X.

EXAMPLE 2

3,3-Dimethyl-2-butyl ester

By a procedure similar to that of Example 1, the 3,3-dimethyl-2-butyl ester was synthesized by using 3,3-dimethyl-2-butanol (Aldrich) in place of (−)-alpha-fenchol. M.P. 126°–128° C. $[\alpha]_D = -20.0°$ (c 1.0, methanol). Sweetness intensity: 30X.

EXAMPLE 3

2,6-Dimethylcyclohexyl ester

By a procedure similar to that of Example 1, the 2,6-dimethylcyclohexyl ester was synthesized by using 2,6-dimethylcyclohexanol (Aldrich, mixture of cis and trans isomers) in place of (−)-alpha-fenchol. M.P. 188°–191° C. $[\alpha]_D = -74.3°$ (c 0.9, methanol). Sweetness intensity: 210X.

EXAMPLE 4

2,5-Dimethylcyclopentyl ester

By a procedure similar to that of Example 1, the 2,5-dimethylcyclopentyl ester was synthesized by using 2,5-dimethylcyclopentanol in place of (−)-alpha-fenchol. The alcohol was prepared by LiAlH$_4$ reduction of 2,5-dimethylcyclopentanone (Aldrich, mixture of cis and trans isomers). M.P. 178°–179° C. $[\alpha]_D = -75.7°$ (c 1.0, methanol). Sweetness intensity: 370X.

EXAMPLE 5

(±) endo-Norbornyl ester

By a procedure similar to that of Example 1, the (±)-endo-norbornyl ester was synthesized by using (±)-endo-norbornyl alcohol (Aldrich) in place of (−)-alpha-fenchol. M.P. 77°–79° C. $[\alpha]_D = -15.7°$ (c 1.0, methanol). Sweetness intensity: 20X

EXAMPLE 6

(±) exo-Norbornyl ester

By a procedure similar to that of Example 1, the (±)-exo-norbornyl ester was synthesized by using (±)-exo-norbornyl alcohol (Aldrich) in place of (−)-alpha-fenchol. M.P. 130°–150° C. $[\alpha]_D = -51.6°$ (c 1.0, methanol). Sweetness Intensity: 150X In certain instances, use of carbobenzyloxy protected D-phenylglycine can cause partial racemization at the asymmetric carbon of the phenylglycine moiety during formation of ester 2. Racemization can be minimized by using o-nitrophenylsulfenyl (o-Nps) protected D-phenylglycine to form ester 2 according to the following reactions:

Ester 2 can be converted to the desired ester 5 by the previously described procedure.

Synthesis of specific esters 5 using o-nitrophenylsulfenyl protected D-phenylglycine are as follows:

EXAMPLE 7

(−)-alpha-Fenchyl ester

Step 1: o-Nitrophenylsulfenyl-D-phenylglycine-(−)-alpha-fenchyl ester a: o-Nitrophenylsulfenyl-D-phenylglycine D-phenylglycine (51 g., 0.34 moles, Aldrich) was dissolved in 180 ml. of 2N NaOH and 200 ml. of dioxane. Then o-nitrophenylsulfenyl chloride (64 g., 0.34 moles) was added in small portions over 1 hour with simultaneous addition of 180 ml. of 2N NaOH. The reaction mixture was stirred for 2 hours and then diluted with 500 ml. of H$_2$O. The mixture was filtered and the solids washed with H$_2$O. The filtrate was acidified with H$_2$SO$_4$ and then extracted three times with ether. The combined extracts were successively washed with H$_2$O and brine, dried over Na$_2$SO$_4$ and then evaporated. The crude product was then recrystallized from ethyl acetate/hexane. Yield: 64.5 g. The purified product was characterized by NMR. $[\alpha]_D = -179.5°$ (c 0.4, methanol).

b. o-Nitrophenylsulfenyl-D-phenylglycine-(−)-alpha-fenchyl ester

The purified o-Nps-D-phenylglycine from step 1a (4 g., 0.015 moles) and (−)-alpha-fenchol (2.3 g., 0.015 moles) were dissolved in 50 ml. of CH$_2$Cl$_2$ and cooled to −65° C. N,N'-dicyclohexylcarbodiimide (3.7 g., 0.018 moles) was added and the mixture then stirred for 20 minutes. A catalytic amount of 4-dimethylaminopyridine (73 mg.) was added and then this reaction mixture was stirred at −65° C. for 1 hour. The reaction mixture was then gradually warmed to −23° C. (carbon tetrachloride/ice bath) and stirred for 3 hours. The mixture was then filtered and the filtrate washed successively with H$_2$O, 2% Na$_2$CO$_3$, H$_2$O, and brine. The washed filtrate was dried over MgSO$_4$, filtered and then evaporated to give 7.0 g. of crude product which was characterized by NMR.

Step 2: D-Phenylglycine-(−)-alpha-fenchyl ester

The crude o-Nps-D-phenylglycine-(−)-alpha-fenchyl ester from step 1b (7 g., 0.017 moles) was dissolved in 50 ml. of acetone and 5N HCl (3.25 ml.) was added. The reaction mixture was stirred for 3 hours and then the acetone was evaporated. The residue was dissolved in 0.1N HCl, was extracted with ether to remove non-basic impurities and was then adjusted to pH 10 with NaOH. The alkaline solution was extracted with ethyl acetate 3 times. The combined extracts were successively washed with H₂O and brine, dried over MgSO₄, and then evaporated to give the desired ester. Yield: 1.0 g. $[\alpha]_D = -94.5°$ (c 2.0, methanol). Higher yields of the ester can be obtained when step 2 is conducted for the minimum time required as determined by thin layer chromatography (generally less than 15 minutes).

Step 3: beta-Benzyl-N-carbobenzyloxy-L-aspartyl-D-phenylglycine-(−)-alpha-fenchyl ester By a procedure similar to that of Example 1, Step 3, the ester from step 2 was converted to the diprotected L-aspartyl-D-phenylglycine-(−)-alpha-fenchyl ester. $[\alpha]_D = -63.3°$ (c 0.4, methanol)

Step 4: alpha-L-Aspartyl-D-phenylglycine-(−)-alpha-fenchyl ester

By a procedure similar to that of Example 1, Step 4, the diprotected ester from step 3 was converted to the desired sweetener. M.P. 176°–177° C. $[\alpha]_D = -103.2°$ (c 0.5, methanol). HPLC analysis showed a single diastereomer. Sweetness intensity: 1750X

EXAMPLE 8a (−)-beta-Fenchyl ester

Step 1: (−)-beta-Fenchol (+)-Fenchone (50 g., 0.33 moles, Fluka, $[\alpha]_D = +65.5°$ (c 5.0, ethanol)) was dissolved in 225 ml. of dry toluene and aluminum isopropoxide (67 g., 0.33 moles) was then added. The mixture was refluxed for 5 days. On days 3, 4 and 5, toluene was allowed to distill off to remove any isopropanol formed; the solvent volume was maintained by the addition of fresh dry toluene. More aluminum isopropoxide (50 g.) was added and the reaction was continued as described above for 2 more days.

Although a significant amount of fenchone remained, the reaction mixture was worked up as follows: the reaction mixture was evaporated to dryness and the solid white residue was taken up in 1000 ml. of 2N HCl. This cloudy solution was extracted 3 times with ether. The combined extracts were washed with H₂O and brine, dried over MgSO₄ and evaporated to give 48 g. of product. Analysis by VPC (30 m.×0.32 mm. J&W DB-1 fused silica column, program 60° to 90° C. at 5° C./min.) showed a 41/26/33 ratio of (+) fenchone/(−)-alpha-fenchol/(−)-beta-fenchol. The (−)-beta-fenchol was isolated by preparative liquid chromatography (Waters Prep 500 with two PrepPak 500 silica columns) using methyl tert-butyl ether/hexane (14/86) as the eluting solvent. Two passes afforded 94% pure (−)-beta-fenchol (beta/alpha=94/6). $[\alpha]_D = -25.7°$ (c 4.9, methanol).

Step 2: alpha-L-Aspartyl-D-phenylglycine-(−)-beta-fenchyl ester

By a procedure similar to that of Example 7, 3.6 g of (−)-beta-fenchol was converted to 1.6 g. of the desired sweetener. Sweetness intensity: 600X

EXAMPLE 8b:

(+)-Beta-fenchyl ester

Step 1: (+)-beta-Fenchol

By the procedure of Example 8a, Step 1, 50 g. of (−)-fenchone (Aldrich, $[\alpha]_C = -51.1°$ (c 5.4, ethanol)) was converted to 45 g. of crude product which was a 52/16/32 mixture of (−)-fenchone/(+)-alpha-fenchol/(+)-beta-fenchol.

An alternative catalytic procedure was also used. Copper chromite (0.5 g.) in 25 ml. of methanol was activated by heating to 125° C. under 1600 psi of H₂ for 10 minutes. After cooling, (−)-fenchone (10 g., 0.066 moles) in 25 ml. of methanol was added. The reaction mixture was heated at 175° C. under a hydrogen pressure of 2900 psi for 19 hours. The reaction mixture was cooled, the catalyst filtered off, and the methanol evaporated to yield 8.7 g. of product. Analysis by VPC (see Example 8a) showed a 3/61/37 ratio of (−)-fenchone-/(+)-alpha-fenchol/(+)-beta-fenchol.

Chromatography of these two fenchone/fenchol mixtures according to Example 8a yielded 96.8% pure (+)-beta-fenchol (beta/alpha=96.8/3.2). $[\alpha]_D = +22.8°$ (c 4.2, methanol).

Step 2: alpha-L-Aspartyl-D-phenylglycine-(+)-beta-fenchyl ester

By procedure similar to that of Example 7, 3.8 g. of (+)-beta-fenchol was converted to 1.1 g. of the desired sweetener. Sweetness intensity: 5000X.

EXAMPLE 9

2,2,4,4-Tetramethylthietan-3-yl ester

Step 1: o-Nitrophenylsulfenyl-D-phenylglycine-2,2,4,4-tetramethylthietan-3-yl ester a. 2,2,4,4-Tetramethylthietan-3-one By following the procedure described in Example 15 of U.S. Pat. No. 4,411,925, 2,2,4,4-tetramethylthietan-3-one was prepared. Yield: 8.0 g.

b. 2,2,4,4-Tetramethylthietan-3-ol

The ketone from step 1a (8.0 g., 0.055 moles) in 20 ml. of ether was added dropwise to a suspension of LiAlH₄ (2.3 g., 0.058 moles) in ether (80 ml.) at 0° C. The reaction mixture was stirred for 3 hours and was then worked up by a procedure similar to that for Example 1, Step 1b to provide 2,2,4,4-tetramethylthietan-3-ol. Yield: 7.0 g.

c. o-Nitrophenylsulfenyl-D-phenylglycine-2,2,4,4-tetramethylthietan-3-yl ester

By a procedure similar to that of Example 7, Step 1b, the o-nitrophenylsulfenyl-D-phenylglycine-2,2,4,4-tetramethylthietan-3-yl ester was prepared using the thietan-3-ol from step 1b. Yield: 5.6 g.

Step 2: D-Phenylglycine-2,2,4,4-tetramethylthietan-3-yl ester

By a procedure similar to that of Example 7, Step 2, the D-phenylglycine-2,2,4,4-tetramethylthietan-3-yl ester was prepared from the thietan-3-yl ester of step 1c. Yield: 2.45 g. $[\alpha]_D = -49.3°$ (c 5.4, methanol).

Step 3: alpha-L-Aspartyl-D-phenylglycine-2,2,4,4-tetramethylthietan-3-yl ester

The thietan-3-yl ester from step 2 (2.45 g, 0.0033 moles) was dissolved in 40 ml. of THF and cooled to 0° C. N-thiocarboxy-L-aspartic anhydride (1.53 g, 0.0088 moles) prepared by the procedure described in Vinick et al, *J. Org. Chem.*, Vol. 47, (1982), p, 2199 et seq. was dissolved in THF and then added to the cooled ester solution. The reaction mixture was stirred for 4 hours and then placed in a freezer overnight. The THF was evaporated and the crude product chromatographed on silica gel with methanol/chloroform/acetic acid/water (23/75/1/2) to give 2.2 g. of the sweetener. The sweetener can be recrystalllized from ethyl acetate/hexane or THF/hexane. Identity of the sweetener was confirmed by NMR, IR and mass spectroscopy. M.P. 169√-170° C. $[\alpha]_D = -44.6$ (c 4.5, methanol).

The alpha-L-aspartyl-D-phenylglycine amides of the present invention can also be synthesized according to the previously described schemes for the esters by using a primary amine R'NH$_2$ instead of the alcohol. Amines R'NH$_2$ used in this synthesis are commercially available or else can be obtained by art recognized methods. See U.S. Pat. No. 4,411,925 to Brennan et al., issued Oct. 25, 1983 (herein incorporated by reference), especially column 12, line 55 to column 20, line 9.

Syntheses of specific alpha-L-aspartyl-D-phenylglycine amides according to this reaction scheme are as follows:

EXAMPLE 10

2,6-Dimethylcyclohexyl amide

By a procedure similar to that of Example 1, the 2,6-dimethylcyclohexyl amide was synthesized using 2,6-dimethylcyclohexylamine obtained from 2,6-dimethylcyclohexonone (Aldrich, mixture of cis and trans isomers) according to the oxime procedure described in Example 47 of U.S. Pat. No. 4,411,925. The amide was too insoluble for an accurate sweetness intensity measurement.

EXAMPLE 11

2,2,4,4-Tetramethylthietan-3-yl amide

Step 1: 2,2,4,4-Tetramethylthietan-3-yl amine

The 2,2,4,4-tetramethylthietan-3-one of Example 9, Step 1a, was converted to the corresponding oxime using hydroxylamine hydrochloride and sodium acetate by the procedure described in Example 12B of U.S. Pat. No. 4,411,925. The oxime (12.0 g., 0.045 moles) in 50 ml. of THF was added dropwise to a stirred suspension of LiAlH$_4$ (6 g., 0.15 moles) in 50 ml. of THF at 0° C. After addition of the oxime was completed, the reaction mixture was allowed to warm to room temperature and was then refluxed for 1.5 hours. The reaction was carefully quenched by dropwise addition of 6 ml. of H$_2$O, 6 ml. of 15% NaOH and 18 ml. of H$_2$O. The quenched solution was filtered and the filtrate evaporated to give 8 g. of crude amine. The crude amine was purified by silica gel chromatography with 5% methanol/chloroform as the eluting solvent. Yield: 3.8 l g.

Step 2: D-Phenylglycine-2,2,4,4-tetramethylthietan-3-yl amine

The purified amine from step 1 (3.1 g., 0.021 moles) was coupled with o-Nps-D-phenylglycine (5.8 g., 0.021 moles) by the procedure of Example 7, Step 1b. D-phenylglycine-2,2,4,4-tetramethylthietan-3-yl amide was obtained from this coupled product by the procedure of Example 7, Step 2. Yield: 1.0 g. M.P. 116°-117° C. $[\alpha]_D = -61.8°$ (c 0.5, methanol)

Step 3: alpha-L-Aspartyl-D-phenylglycine-2,2,4,4-tetramethylthietan-3-yl amide

The D-phenylglycine-2,2,4,4-tetramethylthietan-3-yl amide from step 2 (1.0 g., 0.0036 moles) was coupled with N-thiocarboxyl-L-aspartic acid anhydride according to the procedure of Example 9, Step 3. The crude sweetener obtained was purified by silica gel chromatography using methanol/chloroform/acetic acid/water (65/35/1/1) followed by reverse phase chromatography (Lobar LiChRoprep ™ RP-8) with methanol/H$_2$O (75/25). Identity of the sweetener was confirmed by NMR, IR and mass spectroscopy. Yield: 0.17 g. M.P. 179°-180° C. $[\alpha]_D = -77.6°$ (c 0.3, methanol). Sweetness intensity: 100X based on informal panel testing.

The amides of the present invention can also be synthesized according to the following alternative 4-step reaction scheme:

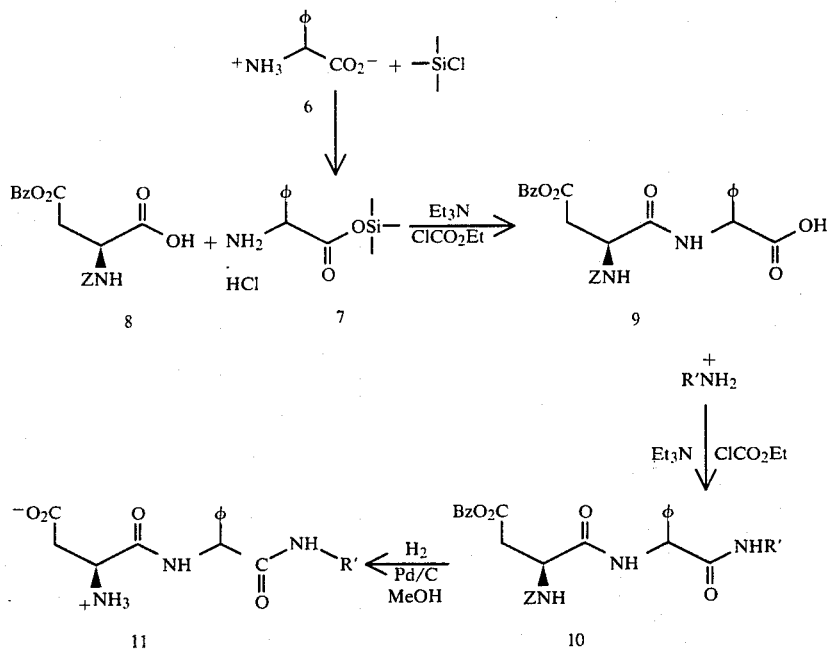

In the first step, D-phenylglycine 6 is reacted with trimethylsilylchlorided to form the silyl ester 7. In the second step, silyl ester 7 is coupled to diprotected L-aspartic acid ester 8 using triethylamine and ethyl chloroformate to form diprotected amide 9. In the third step, amine R'NH$_2$ is coupled to diprotected amide 9 using triethylamine and ethyl chloroformate to form diprotected amide 10. In the fourth step, the protecting groups are removed by hydrogenation of amide 10 over palladium to yield sweetener 11.

The synthesis of one such amide according to this alternative reaction scheme is as follows:

EXAMPLE 12

Dicyclopropylcarbinyl amide

Step 1: D-phenylglycine-trimethylsilyl ester

D-phenylglycine (5.0 g., 0.034 moles, Aldrich) was added to 33 ml. of dry dimethylformamide (DMF). Trimethylsilylchloride (4.5 ml., 0.035 moles) was added and the reaction mixture was stirred until homogeneous.

Step 2: beta-Benzyl-N-carbobenzyloxy-L-aspartyl-D-phenylglycine

In a separate flask, beta-benzyl-N-carbobenzyloxy-L-aspartic acid (6.0 g., 0.017 moles) was dissolved in 20 ml. of DMF and 25 ml. of THF. Triethylamine (2.6 ml., 0.018 moles) was added and the mixture cooled to 0° C. Ethyl chloroformate (1.8 ml., 0.018 moles) was then added and this mixture stirred for 20 minutes. The D-phenylglycine-trimethylsilyl ester mixture from step 1 was added to this stirred mixture. Triethylamine (4.7 ml., 0.034 moles) was then added and the reaction mixture was stirred overnight at room temperature. The triethylamine hydrochloride was filtered off and the precipitate then washed with THF. The filtrate was diluted with 0.2N HCl and then extracted 4 times with chloroform. The combined extracts were washed 5 times with 1N HCl, once with brine, and then dried over $MgSO_4$. The dried extracts were evaporated to give a clear brown liquid. This crude product was crystallized from ether/hexane to give 6.5 g. of the diprotected L-aspartyl-D-phenylglycine containing traces of DMF.

Step 3: beta-Benzyl-N-carbobenzyloxy-L-aspartyl-D-phenylglycinedicyclopropylcarbinyl amide Diprotected L-aspartyl-D-phenylglycine from step 2 (1.0 g., 0.002 moles) was dissolved in 20 ml. of dry THF. This mixture was cooled to 0° C. and then triethylamine (0.23 g., 0.0022 moles) and ethyl chloroformate (0.24 g., 0.0022 moles) were added. This mixture was stirred for 20 minutes, cooled to −35° C. and then dicyclopropylmethylamine (0.23 g., 0.002 moles) prepared according to the procedure described in Example 5 of U.S. Pat. No. 4,411,925 was added as a solution dissolved in THF. The reaction mixture was allowed to warm to room temperature and was then stirred overnight. The reaction mixture was poured into $H_2O$ and then extracted twice with ethyl acetate. The combined extracts were washed successively with 5% $NaHCO_3$, 1N HCl and brine, and then dried over $MgSO_4$. The dried extracts were then evaporated and the crude product purified by silica gel chromatography with ethyl acetate/hexane (50/50) to give 0.8 g. of the purified product. This purified product was characterized by NMR and IR spectroscopy. M.P. 194°–196° C. $[\alpha]_D = -40.2$ (c 0.4, methanol).

Step 4: alpha-L-Aspartyl-D-phenylglycinedicyclopropylcarbinyl amide

The diprotected amide from step 3 was dissolved in methanol/ethyl acetate containing 5% palladiam in charcoal (40 mg.). This mixture was placed in a Parr hydrogenator at 50 psi overnight. The catalyst was then filtered off and the solvent evaporated. The crude product was recrystallized from methanol/$H_2O$, dissolved in hot methanol and then filtered. The methanol was evaporated to give the desired sweetener. Yield: 83 mg. The identity of this sweetener was confirmed by NMR, IR and mass spectroscopy. M.P. 226°–227° C. Sweetness intensity: 80X.

The alpha-L-aspartyl-D-p-hydroxyphenylglycine esters of the present invention can be synthesized according to the following 5-step reaction scheme:

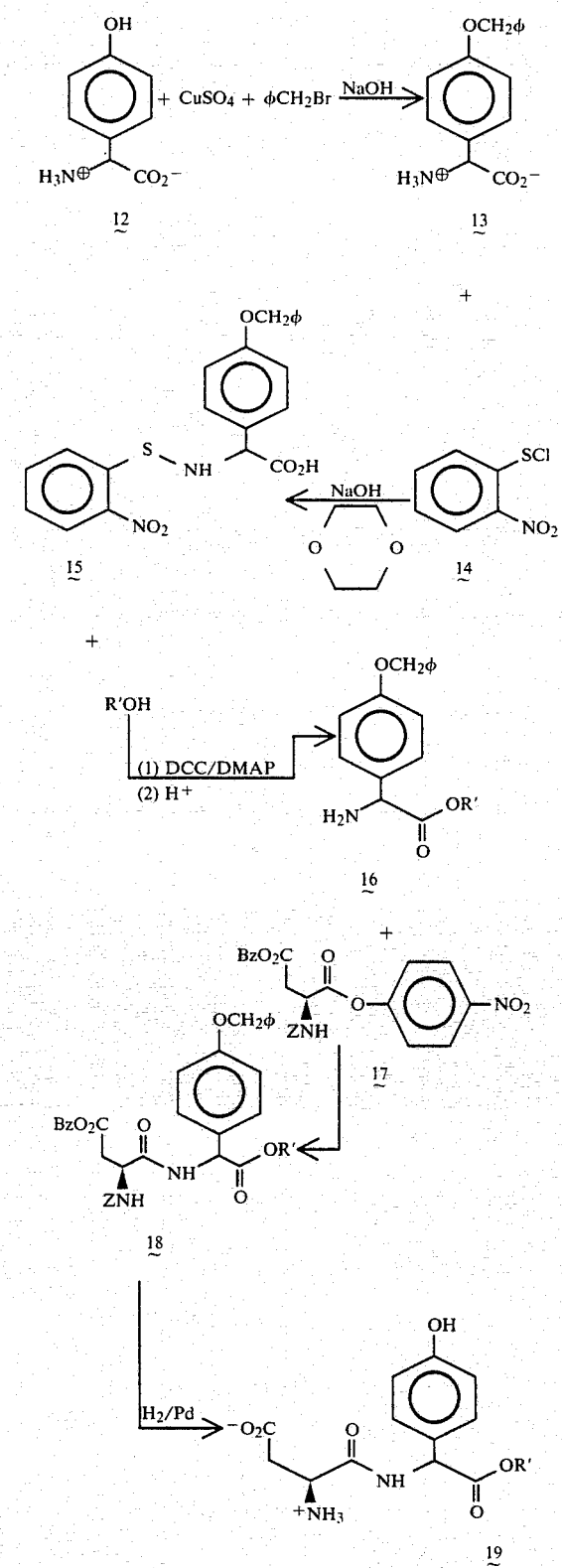

In the first step, D-p-hydroxyphenylglycine 12 is converted to the benzyloxy amino acid 13 by using benzyl bromide and CuSO$_4$. In the second step, amino acid 13 is reacted with o-nitrophenylsulfenyl chloride (o-Nps) to form o-Nps protected ether 15. In the third step, alcohol R'OH is coupled to o-Nps protected ether 15 using DCC/DMAP to form ester 16. In the fourth step, ester 16 is coupled to the protected activated L-aspartic ester 17 to form protected L-aspartyl-D-p-benzyloxyphenylglycine ester 18. In the fifth step, the protecting groups are removed by hydrogenation over palladium to yield sweetener 19.

Synthesis of a specific alpha-L-aspartyl-D-p-hydroxyphenylglycine ester is as follows:

EXAMPLE 13 alpha-L-Aspartyl-D-p-hydroxyphenylglycine-(—)-alpha-fenchyl ester

Step 1: D-p-Benzyloxyphenylglycine

D-p-Benzyloxyphenylglycine was prepared from D-p-hydroxyphenylglycine according to the procedure described in Kamiya et al, Tet., Vol. 35, (1979), p. 323.

Step 2: o-Nitrophenylsulfenyl-D-p-Benzyloxyphenylglycine

D-p-Benzyloxyphenylglycine from step 1 (10.0 g., 0.039 moles) was dissolved in a mixture of 21.4 ml. of 2N NaOH and 50 ml. of dioxane. o-Nitrophenylsulfenyl chloride (7.4 g., 0.039 moles) was then added in portions over 15 minutes while adding another 21.4 ml. of 2N NaOH dropwise. The reaction mixture was stirred for 2 hours, diluted with 50 ml. of H$_2$O and then filtered. The filtrate was acidified with 1N H$_2$SO$_4$ and the resulting solution extracted 5 times with ether. The combined extracts were washed with H$_2$O, dried over Na$_2$SO$_4$, filtered and then evaporated to give 11 g. of product which was characterized by NMR and IR spectroscopy. M.P. 50° C. $[\alpha]_D = +154.9°$ (c 0.7, methanol.)

Step 3a: o-Nitrophenylsulfenyl-D-p-benzyloxyphenylglycine-(—)-alpha-fenchyl ester o-Nps-D-p-benzyloxyphenylglycine from step 2 was reacted with (—)-alpha-fenchol according to Example 7, Step 1b. to form the desired fenchyl ester.

Step 3b: D-p-benzyloxyphenylglycine-(—)-alpha-fenchyl ester

The o-Nps-D-p-benzyloxyphenylglycine-(—)-alpha-fenchyl ester from step 3a was converted to the D-p-benzyloxyphenylglycine-(—)-alpha-fenchyl ester according to Example 7, Step 2 with the following modifications: On partitioning the crude product between 0.1N HCl and ether, most of the desired product was found in the ether layer. This desired product, along with product obtained on ether extraction of the aqueous layer after adjusting the pH to about 10, was chromatographed on silica gel with ethyl acetate/hexane (50/50). $[\alpha]_D = -46.9°$ (c 0.5, methanol).

Step 4 and 5: alpha-L-Aspartyl-D-p-hydroxyphenylglycine-(—)-alpha-fenchyl ester

The D-p-benzyloxyphenylglycine-(—)-alpha-fenchyl ester from step 3b was converted to the desired sweetener according to Example 1, Steps 3 and 4. The sweetener was purified by reverse phase column chromatography with methanol/water (60/40) and was characterized by NMR and IR spectroscopy. M.P. 162° C. $\lambda]_D = -66.1°$ (c 0.38, methanol). Sweetness intensity: 500x The oxa-fenchyl esters and amides of alpha-L-aspartyl-D-phenylglycine can be synthesized by using the respective oxa-fenchol or oxa-fenchyl amine made according to the process disclosed in U.S. application Ser. No. 630,464 to John M. Gardlik, filed July 13, 1984 (Case 3295) (herein incorporated by reference). This process involves the following 4-step reaction scheme:

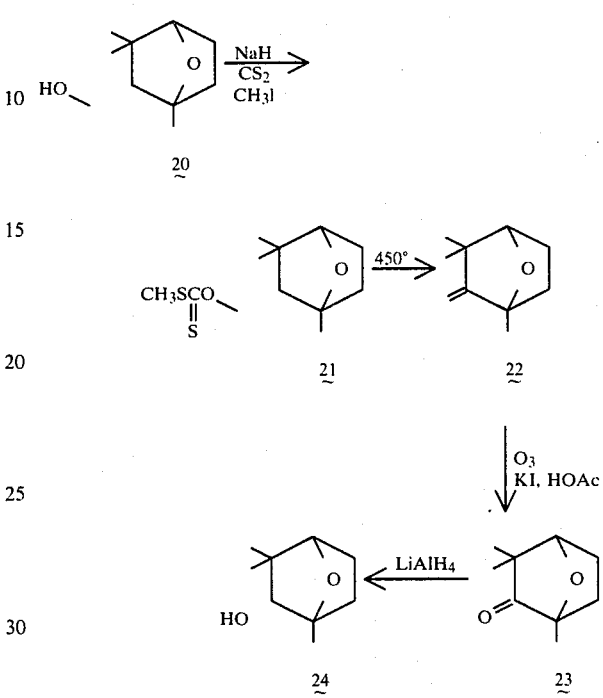

In the first step, alcohol 20 is converted to the xanthate ester 21 by using NaH, carbon disulfide and methyl iodide. In the second step, xanthate ester 21 is thermally decomposed to the methylene substituted bicyclic compound 22. In the third step, bicyclic compound 22 is converted to ketone 23 by using ozone, KI and acetic acid. In the fourth step, ketone 23 is reduced to alcohol 24.

Bicyclic alcohols containing heteroatoms other than oxygen can be synthesized according to art recognized methods. See Tabushi et al., Bull, Chem. Soc. Jap., 51 (4), (1978), pp. 1178–82, and Tabushi et al., J. Am. Chem. Soc., 97 (10), (1975), pp. 2886–91 (herein incorporated by reference), which disclose the preparation of 7-thiabicycloheptanols and dioxide derivatives thereof. See also U.S. Pat. No. 4,353,922 to Pfister, issued Oct. 12, 1982 (herein incorporated by reference), which discloses the preparation of 7-aza-bicycloheptanol derivatives.

The synthesis of the oxa-fenchyl ester using o-nitrophenylsulfenyl protected D-phenylglycine is as follows:

EXAMPLE 14:

alpha-7-oxa-Fenchyl ester

Step 1: o-Nitrophenylsulfenyl-D-phenylglycine-(—)-alpha-7-oxa-fenchyl ester a: o-Nitrophenylsulfenyl-D-phenylglycine o-Nitrophenylsulfenyl-D-phenylglycine was prepared according to the procedure of Example 7, Step 1a.

b: (±)-alpha-7-oxa-fenchol (1): (±)-endo-1,3,3-Trimethyl-7-oxabicyclo[2.2.1]heptane-2-methanol Geraniol was converted to (±)-endo-1,3,3-trimethyl-7-oxabicyclo[2.2.1]heptane-2-methanol using thallium (III) perchlorate according to the procedure described in Yamada et al., *J. Chem. Soc. Chem. Comm.*, (1976), page 997.

(2): S-methyl xanthate ester of (±)-endo-1,3,3-trimethyl-7-oxabicyclo[2.2.1]heptane-2-methanol (±)-endo-1,3,3-Trimethyl-7-oxabicyclo[2.2.1]heptane-2-methanol from step (1) (2.1 g, 0.013 moles) was slowly added to a suspension of NaH (0.90 g., 0.038 moles) in 100 ml. of THF at 0° C. under argon. After stirring at 0° C. for 5 minutes, the reaction mixture was refluxed for 2 hours. Carbon disulfide (2.9 g., 0.038 moles) was added dropwise and the reaction mixture was refluxed for 1 hour. Methyl iodide (5.35 g., 0.037 moles) was then added dropwise and the reaction mixture was refluxed for an additional 2 hours. At this point, the reaction mixture was cooled to room temperature, $H_2O$ was slowly added until two phases formed, the layers were separated, and the aqueous layer was extracted with ether. The organic layers were combined, washed successively with $H_2O$ and brine, and then dried over $MgSO_4$. Evaporation of the solvent and vacuum distillation of the residue afforded the xanthate ester as an amber oil. Yield: 2.78 g. The distilled product was characterized by NMR.

(3): (±)-1,3,3-Trimethyl-2-methylidine-7-oxabicyclo[2.2.1]heptane

The xanthate ester from step (2) (2.78 g, 0.011 moles) was pyrolyzed in the vapor phase at 450° C., 0.1 mm. pressure using a glass tube packed with glass beads heated by a cylindrical furnace. The product was collected using two traps connected in series, both cooled to −78° C. Yield: 1.27 g. The crude product was characterized by NMR.

(4) (±)-1,3,3-Trimethyl-7-oxabicyclo[2.2.1]heptane-2-one

A stream of 3–5% ozone in oxygen was passed through a solution of (±)-1,3,3-trimethyl-7-oxabicyclo[2.2.1]heptane from step (3) (1.20 g., 0.007 moles) in 35 ml. of methanol at −78° C. until the solution became light blue (ozone saturation). The excess ozone was removed by purging the cold reaction mixture with oxygen for 15 minutes. The cold reaction mixture was then poured into a stirred solution of 15 ml. of methanol, 4 ml. of glacial acetic acid, and 8 g. of sodium iodide and stirred for 30 minutes. Sodium thiosulfate solution (0.1N) was added to decompose the liberated iodine. Saturated $NaHCO_3$ solution was then added until the mixture was slightly basic (pH 7.5). The aqueous mixture was extracted with ether, the extract washed with brine, and then dried over $Na_2SO_4$. Evaporation of the solvent afforded the product which was characterized by NMR. Yield: 1.12 g.

(5): (±)-endo-2-Hydroxy-1,3,3-trimethyl-7-oxabicyclo[2.2.1]-heptane ((±)-alpha-7-oxa-fenchol)

A 1M solution of $LiAlH_4$ in ether (15 ml., 0.015 moles) was added dropwise to a solution of (±)-1,3,3-trimethyl-7-oxabicyclo[2.2.1]-heptane-2-one from step (4) (1.10 g., 0.006 moles) in 50 ml. of THF at 0° C. The reaction mixture was stirred for 30 minutes and then quenched by the careful addition of saturated $Na_2SO_4$ solution. The resulting white precipitate was removed by vacuum filtration and washed with ether. The filtrate was evaporated, affording the product as a colorless oil which was characterized by NMR. Yield: 0.82 g.

c. o-Nitrophenylsulfenyl-D-phenylglycine-(±)-alpha-7-oxa-fenchyl ester

The purified o-Nps-D-phenylglycine from step 1a (1.44 g., 0.005 moles) and (±)-alpha-7-oxa-fenchol from step 1b (0.74 g., 0.005 moles) were reacted according to the procedure of Example 7, Step 1b to form the crude o-nitrophenylsulfenyl-D-phenylglycine-(−)-alpha-7-oxa-fenchyl ester. The crude product was purified by flash chromatography on silica gel using 25% ethyl/acetate/hexane as the eluting solvent. The purified ester was characterized by NMR.

Step 2: D-phenylglycine-(±)-alpha-7-oxa-fenchyl ester

The purified o-Nps-D-phenylglycine-(−)-alpha-fenchyl ester from step 1c (1.10 g., 0.025 moles) was converted to the D-phenylglycine-(±)-alpha-7-oxa-fenchyl ester by the procedure of Example 7, Step 2. The ester was characterized by NMR. Yield: 0.55 g.

Step 3: beta-Benzyl-N-carbobenzyloxy-L-aspartyl-D-phenylglycine-(±)-alpha-7-oxa-fenchyl ester By a procedure similar to that of Example 1, Step 3, the ester from step 2 was converted to the diprotected L-aspartyl-D-phenylglycine-(−)-alpha-fenchyl ester. Identity of the ester was confirmed by NMR.

Step 4: alpha-L-Aspartyl-D-phenylglycine-alpha-7-oxa-fenchyl ester

By a procedure similar to that of Example 1, Step 4, the diprotected ester from Step 3 was converted to a mixture of diastereomers from which the desired sweetener (either (+) or (−) oxa-fenchyl ester) was isolated by semi-preparative high performance liquid chromatography using a Whatman Magnum 9 ODS-3 column and 0.01M ammonium acetate in methanol/$H_2O$ (50/50), pH adjusted to 5.4 with acetic acid, as the eluting solvent. The sweetener identity was confirmed by NMR. Sweetness intensity: approximately 1000X based on informal panel testing.

The alpha-L-aspartyl-D-heteroaromatic-substituted glycine esters of the present invention can be synthesized according to the following general reaction scheme:

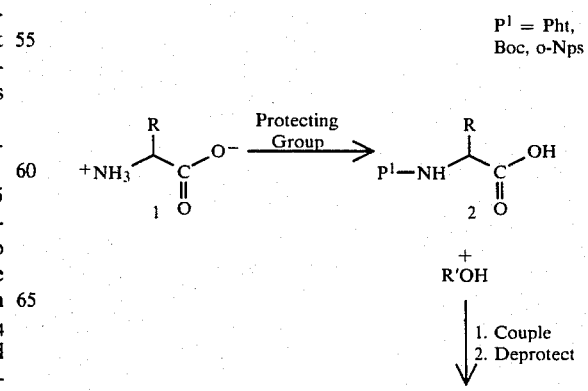

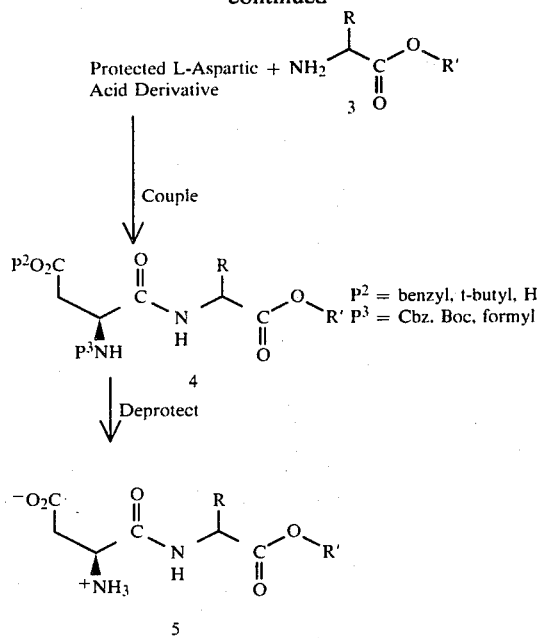

In the first step, D,L-heteroaromatic-substituted glycine 1 is N-protected with a suitable group such as phthaloyl (Pht), t-butoxycarbonyl (Boc) or o-nitrophenylsulfenyl (o-Nps). The protected glycine 2 is then coupled with alcohol R'OH using dicyclohexylcarbodiimide and dimethylaminopyridine or by converting the protected glycine to the respective acid chloride. The coupled product is then deprotected to form ester 3 using hydrazine hydrate (removal of Pht group), trifluoroacetic acid (removal of Boc group) or HCl in aqueous acetone (removal of o-Nps group). Ester 3 is then coupled with a suitable protected activated L-aspartic acid derivative to form protected dipeptide ester 4. Suitable L-aspartic acid derivatives include the mixed anhydride of beta-benzyl-N-benzyloxycarbonyl-L-aspartate ($P^2$=benzyl, $P^3$=Cbz), beta-benzyl-N-benzyloxycarbonyl-L-aspartyl-p-nitrophenyl ester ($P^2$=benzyl, $P^3$=Cbz), beta-t-butyl-N-t-butoxycarbonyl-L-aspartyl-p-nitro-phenyl ester ($P^2$=t-butyl, $P^3$=Boc) and N-formyl-L-aspartic acid anhydride ($P^2$=H, $P^3$=formyl). The protected dipeptide ester 4 is deprotected to form dipeptide ester 5 by catalytic hydrogenalysis (removal of benzyl and Cbz groups), use of HCl (removal of t-butyl group) or use of NH₂OH (removal of formyl group). The dipeptide ester 5 is a mixture of diastereomers which can be separated by preparative HPLC to provide the desired L-aspartyl-D-heteroaromatic-substituted glycine ester sweeteners.

The D,L-heteroaromatic-substituted glycines used in this synthesis are commercially available (e.g., D,L-2-thienylglycine, D,L-3-thienylglycine), can be obtained by methods disclosed in this application (e.g., D,L-2-furylglycine), or else can be obtained by art recognized methods. See U.S. Pat. No. 3,821,207 to Chow et al, issued June 28, 1974 (herein incorporated by reference), especially Column 2, line 48 to Column 5, line 60. See also U.S. Pat. No. 3,920,730 to Gleason et al, issued Nov. 18, 1975 (preparation of N-acyl-alpha-heteroaromatic glycines); Hatanaka et al, *J. Med. Chem.*, 16 (9), (1973), pp. 978–84 (preparation of D,L-thienylglycines, D,L-thiazolylglycines and D,L-isothiazolyglycines); Davis et al, *Arch. Biochem, Biophys.*, 87, (1960), pp. 88–92 (preparation of D,L-pyridylglycines); Jacobson et al, *Acta Chem. Scand.*, B35, (1981), pp 289–94 (preparation of D,L-pyridylglycines); Ricciardi et al, *Org. Prep. Proc. Int.*, 15 (1–2), (1983), pp 17–28 (preparation of D,L-imidazolylglycines); Schneider, *Z. Physiol. Chem.*, 324, (1961), pp 206–10 (preparation of D,L-imidazolylglycines), all of which are incorporated by reference.

The alcohols R'OH used in this synthesis are commercially available (e.g., alpha-fenchol), can be obtained by methods disclosed in the present application (e.g., beta fenchol) or can be obtained by art recognized methods. See U.S. Pat. No. 4,411,925 to Brennan et al, issued Oct. 25, 1983, especially column 12, line 55 to column 20, line 9 (preparation of various branched and cyclic alcohols); Tabushi et al, *Bull. Chem. Soc. Jap.*, 51 (4), pp 1178–82 and Tabushi et al, *J. Am. Chem. Soc.*, 97 (10), (1975), pp. 2886–91 (preparation of 7-thiabicycloheptanols and dioxide derivatives); U.S. Pat. No. 4,353,922 to Pfister, issued Oct. 12, 1982 (preparation of 7-azabicycloheptanol derivatives); U.S. Pat. No. 4,487,945 to Payne, issued Dec. 11, 1984, and U.S. Pat. No. 4,542,244 to Payne et al, issued Sept. 17, 1985, especially column 11, line 34 to column 14, line 57, and U.S. application Ser. No. 630,464 to John M. Gardlik, filed July 13, 1984 (preparation of 7-oxabicycloheptanols), all of which are incorporated by reference.

The alpha-L-aspartyl-D-heteroaromatic-substituted glycine amides of the present invention can also be synthesized according to the previously described scheme for the esters by using a primary amine R'NH₂ instead of the alcohol. Amines R'NH₂ used in this synthesis are commerically available or else can be obtained by art recognized methods. See U.S. Pat. No. 4,411,925 to Brennan et al, issued Oct. 25, 1983 (herein incorporated by reference), especially column 12, line 55 to column 20, line 9, which describes an oxime procedure for obtaining amines R'NH₂ from the respective ketone. The ketones are either commercially available or else can be obtained by oxidation of the respective alcohol R'OH.

Syntheses of preferred alpha-L-aspartyl-D-furylglycine and alpha-L-aspartyl-D-thienylglycine esters and amides according to the present invention are as follows:

EXAMPLE 15 alpha-L-Aspartyl-D,L-2-furylglycine-(+)-alpha-fenchyl ester.

A. D,L-5-(2-Furyl)-hydantoin

A mixture of powdered potassium cyanide (32.6 g, 0.5 mol), ammonium carbonate (96.0 g, 1 mol) and 2-furaldehyde (24.0 g, 0.25 mol) in 50% aqueous ethanol (650 ml) was heated at 55° C. for 6 hrs. after which the solution was concentrated to two-thirds of its initial volume. The solution was cooled in an ice-bath, acidified with concentrated HCl and left at 0° C. until the product crystallized out. Obtained were 22.7 g (0.137 mol, 55% yield) of 5-(2-furyl)-hydantoin as a tan product: mp 145°–146° C.

B. D,L-2-Furylglycine

The 5-(2-furyl)-hydantoin from Step A (22.0 g, 0.133 mol) and barium hydroxide octahydrate (67.3 g, 0.213 mol) were added to 325 ml of boiling water. The mixture was refluxed for 24 hrs., cooled to room temperature, and then the barium carbonate was filtered off. The filtrate was treated again with ammonium carbonate (12.8 g, 0.133 mol) to precipitate the barium remaining in solution. The resulting mixture was refluxed for 5 minutes and filtered. The filtrate was evaporated to dryness. The remaining brown crystals were recrystallized from a 1:2 mixture of water:methanol to give 9.7 g (52% yield) of 2-furylglycine as light beige crystals: mp 195°–199° C.

C. N-Phthaloyl-D,L-2-furylglycine

The 2-furylglycine from Step B (9.08 g, 64.4 mmol) and $Na_2CO_3$ monohydrate (8.6 g, 69.5 mmol) were dissolved in 90 ml of water. N-(ethoxycarbonyl)phthalimide (14.1 g, 64.4 mmol) was then added. The mixture was stirred at room temperature for 1 hr., filtered, and the filtrate cooled to 0° C. The filtrate was acidified with 6N HCl to pH 3. The precipitated product was isolated by filtration and washed with water. Recrystallization from ethyl acetate/hexane gave 12.7 g (73% yield) of N-phthaloyl-2-furylglycine as beige crystals: mp 166°–168° C.

D. N-Phthaloyl-D,L-2-furylglycine-(+)-alpha-fenchyl ester

The N-phthaloyl-2-furylglycine from Step C (13.0 g, 48 mmol) was added to 45 ml of freshly distilled thionyl chloride and the mixture refluxed for 1 hr. Excess thionyl chloride was distilled off and the remaining solid was taken up in 40 ml of dry tetrahydrofuran (THF). The resulting acid chloride (in 70 ml of ether), was added dropwise to a cooled (0° C.) mixture of (+)-alpha-fenchol (41.5 g, 0.269 mol) in ether (40 ml) and pyridine (92 ml). After addition of the acid chloride was complete (20 min.), the reaction mixture was warmed to room temperature and stirred, under argon, for 16 hrs. The pyridine hydrochloride was removed by filtration through a short pad of celite. The filtrate was successively washed with 10% citric acid solution (3×100 ml), 4% $NaHCO_3$ solution (2×100 ml), water (1×100 ml) and brine (1×100 ml). The washed filtrate was dried over $Na_2SO_4$, filtered, and evaporated in vacuo. Excess (+)-alpha-fenchol was removed at reduced pressure (bp 107°–108° C., 30 mm) to give 14.8 g of crude product. This crude product was purified by silica gel column chromatography using a 97:3 mixture of toluene:ethyl acetate as the eluting solvent to give 11.1 g (57% yield) of the protected ester as white crystals: mp 105°–107.5° C.; $[\alpha]_D^{20} = +14.28°$ (c 0.56, dimethylformamide (DMF)).

E. D,L-2-Furylglycine-(+)-alpha-fenchyl ester

To a solution of the protected ester from Step D (10.6 g, 26 mmol) in ethanol (175 ml) was added hydrazine monohydrate (1.6 ml, 33.9 mmol). The homogeneous solution was refluxed for 3 hrs. after which acetic acid (4 ml) was added to destroy any remaining hydrazine. The solution was then cooled, filtered, and the solvent evaporated. The residue was dissolved in 1N HCl (20 ml), washed with ether (2×50 ml), cooled to 0° C. and made basic with conc. NaOH. The basic layer was extracted with ether (5×100 ml). The combined ether extracts were dried over $Na_2SO_4$, filtered and evaporated in vacuo, to give 6.0 g (83.5% yield) of deprotected ester as a clear oil: $[\alpha]_D^{18} = +20.5°$ (c 0.925, DMF).

F. Beta-benzyl-N-(Benzyloxycarbonyl)-L-aspartyl-D,L-2-furylglycine-(+)-alpha-fenchyl ester A reaction vessel equipped with a thermometer, addition funnel, and static argon line was charged with freshly recrystallized beta-benzyl-N-(benzyloxycarbonyl)-L-aspartate (2.42 g, 6.79 mmol) and 50 ml of dry THF. The vessel was cooled to −15° C. by means of a dry ice/ethanol bath and N-methyl morpholine (0.78 ml, 7.08 mmol) was added all at once. The mixture was stirred for 10 min. prior to the dropwise addition of a solution of isobutyl chloroformate (0.94 ml, 7.21 mmol) in 3 ml of dry THF. A white precipitate formed immediately upon the addition of the chloroformate. The reaction mixture was stirred at −15° C. for 50 min. to ensure complete formation of the mixed anhydride prior to the dropwise addition of a solution of the deprotected ester from step E (2.0 g, 7.22 mmol) in 6 ml of dry THF. Upon complete addition of the deprotected ester, the reaction mixture was stirred at −15° C. for 1 hr., slowly warmed to room temperature and then stirred for an additional 30 min. The THF was removed in vacuo and the solid then dissolved in 100 ml of ethyl acetate. The organic solution was successively washed with 1N HCl (2×50 ml), saturated $NaHCO_3$ solution (2×50 ml), and brine (1×50 ml). The washed organic solution was dried over $Na_2SO_4$, filtered, and evaporated in vacuo to give 4.26 g of crude product. Purification via silica gel column chromatography using a 97:3 mixture of chloroform:ethyl acetate as the eluting solvent, gave 3.4 g (76% yield) of the protected dipeptide ester as a clear oil.

G. L-Aspartyl-D,L-2-furylglycine-(+)-alpha-fenchyl ester

To a solution of the protected dipeptide ester from Step F (0.69 g, 1.12 mmol) in methanol (45 ml) was added approximately 0.14 g of 5% Pd on carbon and 7 mg of quinoline. The suspension was hydrogenated on a Parr apparatus at 48 psi for 4.5 hrs. The hydrogenated mixture was filtered and the solvent then removed under reduced pressure. The white solid obtained was then purified by reverse phase preparative HPLC (eluting solvent was 35% aqueous acetonitrile with 0.005M phosphate buffer, pH 6), the eluting solvent evaporated to dryness and the remaining solid extracted with methanol. Evaporation of the methanol extracts produced a white powder which was recrystallized from ether/hexane. Obtained were 0.28 g (64% yield) of the deprotected dipeptide ester as a white amorphous solid: mp 153°–155° C., $[\alpha]_D^{25} = +1.68$ (c 0.6, DMF).

EXAMPLE 16 alpha-L-Aspartyl-D-2-furylglycine-(+)-beta-fenchyl ester

A. N-phthaloyl-D,L-2-furylglycine-(+)-beta-fenchyl ester

To N-phthaloyl-D,L-2-furylglycine (6.0 g, 22 mmol) prepared according to the procedure of Example 15, Step C, in 65 ml of a 3:1 mixture of methylene chloride:THF was added (+)-beta-fenchol (3.41 g, 22 mmol, obtained by reduction of (−)-fenchone with aluminum isopropoxide followed by silica gel chromatography with a 14:86 mixture of methyl t-butyl ether:hexane as eluting solvent). The solution was cooled to −40° C. and dicyclohexylcarbodiimide (5.90 g, 29 mmol) was added followed by dimethylaminopyridine (0.11 g). The reaction mixture was allowed to warm to 0° C. over 3 hrs. The precipitate which formed was filtered off. The filtrate was successively washed with water, 01.N NCl, a 2% Na₂CO₃ solution, water and brine. The washed filtrate was dried over MgSO₄ and evaporated. The crude product obtained was chromatographed on silica gel with 97% toluene/ethyl acetate to give 4.2 g of the N-phthaloyl protected product.

B. D,L-2-furylglycine-(+)-beta-fenchyl ester

The N-phthaloyl protected product from Step A (3.0 g, 7.4 mmol) and hydrazine monohydrate (0.46 ml, 9.4 mmol) in 50 ml of ethanol was refluxed for 2.5 hrs. and then acetic acid (1 ml) was added. The reaction mixture was then cooled, filtered and the solvent evaporated. The residue was dissolved in 1N HCl and extracted with ether. The aqueous layer was made basic with 5N NaOH and then extracted again with ether. The combined ether extracts were dried over Na₂SO₄, and evaporated to give 2.0 g of the deprotected ester.

C. beta-Benzyl-N-benzyloxycarbonyl-L-aspartyl-D,L-2-furylglycine-(+)-beta-fenchyl ester The deprotected ester from Step B (1.8 g, 6.5 mmol) and beta-benzyl-N-benzyloxycarbonyl-L-aspartyl-p-nitrophenyl ester (3.0 g, 6.3 mmol, prepared from beta-benzyl-N-benzyloxycarbonyl-L-aspartic acid (Ba-Chem), p-nitrophenol, dicyclohexylcarbodiimide and dimethylaminopyridine) were stirred overnight at room temperature in 75 ml of dry THF. The THF solvent was evaporated and the residue partitioned between ethyl acetate and water. The organic phase was successively washed with 4% Na₂CO₃ (several times), water and brine. The washed organic phase was dried over MgSO₄ and then evaporated to give 3.5 g of crude product. The crude product was chromatographed with 20% ethyl acetate/isooctane as the eluting solvent to give 2 g of purified protected dipeptide ester.

D. L-aspartyl-D,L-2-furylglycine-(+)-beta-fenchyl ester

The protected dipeptide ester from Step C (1 g) was deprotected according to the procedure of Example 1, Step G. The crude deprotected product was chromatographed on silica gel with a 25:75:1:2 mixture of methanol:chloroform:water:acetic acid as the eluting solvent to give 0.5 g of the purified deprotected dipeptide ester as a diastereomeric mixture.

E. L-aspartyl-D-2-furylglycine-(+)-beta-fenchyl ester

A portion of the diastereoisomeric mixture from Step D was separated by semipreparative HPLC using a Whatman Magnum 9 Partisil 10, ODS-3 column with a 65:35 mixture of methanol:0.01M ammonium acetate, pH 6, as the eluting solvent to give 28 mg of a 94:6 mixture of D-furyl:L-furyl isomers: mp 153° C., $[\alpha]_D^{24} = -63.2°$ (c 0.16, methanol).

EXAMPLE 17 alpha-L-Aspartyl-D,L-2-furylglycine-2,5-dimethylcyclopentyl ester

The procedure of Example 16, Steps A through C, were used to convert N-phthaloyl-D,L-2-furylglycine (1.5 g) to the respective protected dipeptide ester (2.0 g) by substituting 2,5-dimethylcyclopentanol (0.65 g.) for (+)-beta-fenchol. Subsequent deprotection as in Example 1, Step G provided the dipeptide ester as a mixture of diastereomers.

EXAMPLE 18 alpha-L-Aspartyl-D-2-thienylglycine-(+)-beta-fenchyl ester

A. o-Nitrophenylsulfenyl-D,L-2-thienylglycine

D,L-2-thienylglycine (9 g, 57 mmol, Aldrich) was dissolved in 40 ml of dioxane. Half (12 ml) of the required 5N NaOH was added to this solution, followed by o-nitrophenylsulfenyl chloride (14.6 g, 77 mmol) in small portions. The remaining NaOH was added as needed to keep the reaction mixture basic. The reaction mixture was stirred for 2 hrs. and then filtered. The filtrate was acidified with H₂SO₄. The acidified solution was extracted three times with ethyl acetate. The combined ethyl acetate extracts were successively washed with water and brine. The washed extracts were dried over MgSO₄, filtered and evaporated to give 16 g of crude product. This crude product was recrystallized from ethyl acetate/hexane using a small amount of methanol to give 11.4 g of purified protected 2-thienylglycine.

B. D,L-2-thienylglycine-(+)-beta-fenchyl ester

The protected 2-thienylglycine from Step A (7 g, 23 mmol) was coupled with (+)-beta-fenchol (3.5 g, 23 mmol) using dicyclohexylcarbodiimide and dimethylaminopyridine according to the procedure of Example 16, Step A, with THF as the solvent. After standing at room temperature overnight, the reaction mixture was filtered, the solvent evaporated and the residue partitioned between ether and water. The ether phase was successively washed with 0.1N HCl, a 2% Na₂CO₃ solution, water and brine. The washed ether phase was dried over MgSO₄ and evaporated to give 11.5 g of crude product as a dark oil. This oil was chromatographed on silica gel with 60% chloroform/hexane as the eluting solvent to give 3.8 g of purified product. To this purified product (3.8 g, 8.5 mmol) dissolved in 30 ml of acetone (cooled to 0° C.) was added 5N HCl (2.0 ml). The mixture was stirred for 30 min. and the solvent then evaporated. The residue was partitioned between 1N HCl and ether. The aqueous layer was made basic with 1N NaOH and then extracted again with ether. The combined ether extracts were washed with brine, dried over MgSO₄, filtered and then evaporated to give 1.2 g of the deprotected ester.

C. beta-t-butyl-N-t-butoxycarbonyl-L-aspartyl-D,L-2-thienylglycine-(+)-beta-fenchyl-ester The deprotected ester from Step B (0.95 g, 3.2 mmol) was dissolved in 25 ml of THF. beta-t-butyl-N-t-butoxycarbonyl-L-aspartyl-alpha-p-nitrophenyl ester (1.6 g, 3.9 mmol, Bachem) was then added and the reaction mixture was stirred overnight. The solvent was then evaporated, the residue taken up in ether and then successively washed with a Na₂CO₃ solution (several times), water and brine. The washed residue was dried over MgSO₄, filtered and then evaporated. The crude product obtained was chromatographed on silica gel with 15% acetone/hexane as the eluting solvent to give 0.54 g of the purified protected dipeptide ester.

D. L-aspartyl-D,L-2-thienylglycine-(+)-beta-fenchyl ester

The protected dipeptide ester from Step C (216 mg, 0.38 mmol) was dissolved in 25 ml of chloroform. Gaseous HCl was bubbled through the chloroform solution for 15 min. and the reaction mixture was then stirred for 2 hrs. The solvent was evaporated to give 140 mg of crude product containing the deprotected dipeptide ester as a diastereomeric mixture.

E. L-aspartyl-D-2-thienylglycine-(+)-beta-fenchyl ester

A portion of the diastereomeric mixture from Step D was separated by semi-preparative HPLC using a Whatman Magnum 9, Partisil 10, ODS-3 column with a 65:35 mixture of methanol:0.01 M ammonium acetate, pH 6.0, as the eluting solvent to give 43 mg of a 92.5:7.5 mixture of D-thienyl:L-thienyl isomers: mp 179°–180° C., $[\alpha]_D^{24} = -55.4°$ (c 0.065, methanol).

EXAMPLE 19 alpha-L-Aspartyl-D-3-thienylglycine-(+)-beta-fenchyl ester

A. D,L-3-thienyl-(+)-beta-fenchyl ester

Starting with D,L-3-thienylglycine (2.0 g, 12.7 mmol, Aldrich), the (+)-beta-fenchyl ester was prepared (0.55 g) according to the procedure of Example 18, Steps A and B.

B. N-formyl-L-aspartyl-D,L-3-thienylglycine-(+)-beta-fenchyl ester

The (+)-beta-fenchyl ester from Step A (0.40 g, 1.37 mmol) was dissolved in 20 ml of pyridine. N-formyl-L-aspartic acid anhydride (0.30 g, 2.08 mmol, prepared from L-aspartic acid, acetic anhydride and formic acid) was added at 0° C. The reaction mixture was stirred and then allowed to come to room temperature over 3 hrs. Water and methanol were added and then the solvent was evaporated. The residue was partitioned between ethyl acetate and 1N HCl. The organic layer was washed with water and brine. The washed organic layer was dried over MgSO₄, filtered and then evaporated to give a mixture of alpha and beta coupled products. The faster eluting alpha coupled product was isolated by silica gel chromatography with a 10:90:0.5 mixture of methanol:chloroform:acetic acid as the eluting solvent to give 0.24 g of product containing the protected dipeptide ester.

C. L-aspartyl-D,L-3-thienylglycine-(+)-beta-fenchyl ester

The protected dipeptide ester from Step B (0.16 g, 0.37 mmol) was dissolved in 10 ml of a 1:1 mixture of pyridine:water. Hydroxylamine.HCl (120 mg, 1.72 mmol) was added and the reaction was stirred for 2 days at 50° C. The solvent was then evaporated and the residue taken up in ethyl acetate with the solvent again being evaporated. The second residue was chromatographed on silica gel with a 20:80:1:2 mixture of methanol:chloroform:water:acetic acid as the eluting solvent to give 0.15 g of purified product containing the deprotected dipeptide ester as a diastereomeric mixture.

D. L-aspartyl-D-3-thienylglycine-(+)-beta-fenchyl ester

A portion of the diastereomeric mixture from Step C was separated by semi-prepartive HPLC chromatography using a Whatman Magnum 9, Partisil 10, ODS-3 column with a 65:35 mixture of methanol:0.01M ammonium acetate, pH 6.0, as the eluting solvent to give 25 mg of an 86:13 mixture of D-thienyl:L-thienyl isomers.

EXAMPLE 20 alpha-L-Aspartyl-D-2-furylglycine-2,2,4,4-tetramethyl-thietan-3-yl amide.

A. N-t-butoxycarbonyl-D,L-2-furylglycine

D,L-2-furylglycine (4 g, 28.4 mmol from Example 15, Step B) was added to NaOH (2.84 g, 35.2 mmol) in 40 ml of a 1:1 mixture of dioxane:water at 0° C. To the thick mixture was added di-t-butyl dicarbonate (6.82 g, 35.2 mmol). The reaction mixture was stirred for 30 min. and then allowed to come to room temperature. After 5.5 hrs., 50 ml of water was added. The aqueous layer was extracted with ethyl acetate, acidified to pH 3 with 1N HCl and extracted again with ethyl acetate. The ethyl acetate extracts of the acidic aqueous layer were combined, dried over MgSO₄, filtered, and then evaporated to give 2.22 g of protected 2-furylglycine as a brown oil.

B. D,L-2-furylglycine-2,2,4,4-tetramethtylthietane-amide

The protected 2-furylglycine from Step A (1.42 g, 5.88 mmol) and 3-amino-2,2,4,4-tetramethylthietane (0.85 g, 5.88 mmol, prepared according to U.S. Pat. No. 4,411,925, Example 15) were coupled according to the procedure of Example 2, Step A using methylene chloride as the solvent. When worked up, 2.30 g of crude product was obtained as a brown solid. Trituration of the brown solid with 15 ml of cold hexane gave 1.49 of a tan solid. This tan solid (1.49 g, 4.0 mmol) was dissolved in 15 ml of methylene chloride; trifluoroacetic acid (4.56 g, 40 mmol) was then added. The reaction mixture was stirred overnight and then concentrated in vacuo. The residue was dissolved in 0.1N HCl and then extracted with ether. The aqueous layer was made basic (pH 9) with 1N NaOH and then extracted again with ether. The combined ether extracts were washed with brine, dried with Na₂SO₄, filtered and evaporated to give 0.78 g the amide as a tan solid.

C. beta-t-butyl-N-t-butoxycarbonyl-L-aspartyl-D,L-2-furylglycine-2,2,4,4-tetramethylthietane amide The amide from Step B (0.35 g, 1.3 mmol) and beta-t-butyl-N-t-butoxycarbonyl-L-aspartyl-p-nitrophenyl ester (0.53 g, 1.3 mmol, Bachem) were stirred in 15 ml of dry THF for 4 days. The solvent was evaporated and the resulting residue was triturated with 50 ml of ether. The triturate was washed with 4% NaHCO₃ solution and brine, dried over Na₂SO₄, filtered and then evaporated to give 0.52 g of crude product. The crude product was chromatographed on silica gel with 45% methyl t-butyl ether/hexane as the eluting solvent to give 0.33 g of the purified protected dipeptide amide as a pale yellow solid. This reaction was repeated on a similar scale to give an additional 0.57 g of the protected dipeptide amide.

D. L-aspartyl-D,L-2-furylglycine-2,2,4,4-tetramethylthietane amide

The procedure of Example 18, Step D was used to convert the protected dipeptide amide from Step C (0.47 g, 0.9 mmol) to 0.36 g of crude deprotected product. This crude deprotected product was dissolved in 25 ml of water and extracted with chloroform. The aqueous layer was adjusted to pH 5.6 with 0.1N NaOH and again extracted with chloroform. The aqueous layer was then evaporated to dryness to give 0.18 g of a pale yellow solid containing the deprotected dipeptide amide as a diastereomeric mixture.

E. L-aspartyl-D-2-furylglycine-2,2,4,4-tetramethylthietane amide

The diastereomeric mixture from Step D was separated by semi-preparative HPLC using a Whatman Magnum 9, Paritisil 10, ODS-3 column with a 50:50 mixture of methanol: 0.01M ammonium acetate, pH 5.4, as the eluting solvent to give 60 mg of a second eluting fraction. This second eluting fraction contained a 95:3 mixture of D-furyl:L-furyl isomers.

EXAMPLE 21 alpha-L-Aspartyl-D-2-furylglycine-(−)-alpha-fenchyl amide

The procedure of Example 20, Steps B through D was used to convert N-t-butoxycarbonyl-D,L-2-furylglycine (2.75 g, 11.4 mmol) to the respective dipeptide (−)-alpha-fenchyl amide (2.05 g., diastereomeric mixture) by substituting (−)-alpha-fenchyl amine (1.74 g.) for 3-amino-2,2,4,4-tetramethylthietane. The procedure of Example 20, Step E was used to separate the diastereomeric mixture into a 96:4 mixture of D-furyl:L-furyl isomers.

EXAMPLE 22 alpha-L-Aspartyl-D,L-2-furylglycinedicyclopropylcarbinyl amide

The procedure of Example 20, Steps B through D was used to convert N-t-butoxycarbonyl-D,L-2-furylglycine (2.50 g., 10.4 mmol) to the respective dipeptide amide (0.42 g, disteromeric mixture) by substituting dicyclopropylcarbinyl amine (1.15 g, 10.4 mmol) for 3-amino-2,2,4,4-tetramethylthietane. The procedure of Example 20, Step E was used to obtain a 59:38 mixture of D-furyl:L-furyl isomers.

D. Uses of alpha-L-aspartyl-D-phenylglycine and alpha-L-aspartyl-D-hetero-aromatic substituted glycine esters and amides The esters or amides of the present invention can be used to sweeten a variety of edible materials. However, the onset and duration of the sweetness of some of these esters and amides is somewhat slower and more lingering than that of sucrose. As a result, mixtures of these esters or amides with other sweeteners having a quicker onset of sweetness are preferred. In particular, mixtures of these esters or amides with saccharin or non-toxic salts thereof are especially preferred. As used herein, "non-toxic salts of saccharin" means those salts of saccharin with physiologically acceptable cations such as sodium, potassium, calcium or ammonium. The mixtures of the present esters or amides with saccharin can be in a ratio (sweetness equivalent basis) of from about 2:1 to about 1:9, and preferably from about 1:1 to about 1:4. Mixtures of the present esters and amides with other sweeteners having a quicker onset of sweetness can also be used. Examples of such sweeteners include Acesulfam; the alpha-L-aspartyl-L-phenylalanine lower alkyl esters disclosed in U.S. Pat. No. 3,492,131 to Schlatter, issued Jan. 27, 1970 (herein incorporated by reference), in particular the methyl ester known as aspartame; the alpha-L-aspartyl-L-1-hydroxymethylalkyl amides disclosed in U.S. Pat. No. 4,338,346 to Brand, issued July 6, 1982 (herein incorporated by reference); the alpha-L-aspartyl-L-1-hydroxyethylalkyl amides disclosed in U.S. Pat. No. 4,423,029 to Rizzi, issued Dec. 27, 1983 (herein incorporated by reference); the alpha-L-aspartyl-D-alanine amides disclosed in U.S. Pat. No. 4,411,925 to Brennan et al., issued Oct. 25, 1983 (herein incorporated by reference); and the alpha-L-aspartyl-D-serine amides disclosed in U.S. Pat. No. 4,399,163 to Brennan et al., issued Aug. 16, 1983 (herein incorporated by reference). Low calorie mixtures can also be formulated which contain esters or amides of the present invention with sucrose.

The esters and amides of the present invention, including mixtures thereof with other sweeteners, are useful for sweetening a variety of food products, such as fruits, vegetables, juices, cereals, meat products such as ham or bacon, sweetened milk products, egg products, salad dressings, ice creams and sherbets, gelatins, icings, syrups, cake mixes and frostings. In particular, these sweeteners are useful for sweetening a variety of beverages such as lemonade, coffee, tea, and particularly carbonated beverages. The sweeteners of the present invention can also be used to sweeten dentifrices, mouthwashes, and chewing gums, as well as drugs such as liquid cough and cold remedies. As an alternative to direct addition of the esters and amides of the present invention to the foregoing edible materials, sweetener concentrates can be prepared using these esters and amides in, for example, granular or liquid form. These concentrates can then be conventionally metered into foods, beverages and the like as desired by the user.

The esters and amides of the present invention are stable substances that can be used in a variety of physical forms such as powders, granules, tablets, syrups, pastes, solutions and the like. Liquid or solid ingestible carriers such as water, glycerol, starch, sorbitol, salts, citric acid, cellulose and other suitable non-toxic substances can also be used. These sweetening agents can be readily used in pharmaceutical compositions to impart a sweet taste.

The ester and amide sweeteners of the present invention are used in amounts sufficient to provide a sweet taste of the desired intensity for orally ingested products. The amount of the sweetener added will generally depend upon comnercial needs as well as individual sweetness sensitivities.

Specific Embodiments of Oral Products Containing Alpha-L-Aspartyl-D-Phenylglycine Esters

A. Beverage

Mixtures of the (−)-alpha-fenchyl ester of Example 7 with other sweeteners were used in cola beverages that were formulated as follows:

| Ingredients | Embodiment 1 (%) | Embodiment 2 (%) |
|---|---|---|
| H$_3$PO$_4$ | 0.06 | 0.06 |

-continued

| Ingredients | Embodiment 1 (%) | Embodiment 2 (%) |
|---|---|---|
| Caramel color | 0.25 | 0.25 |
| Flavor | 0.0032 | 0.0032 |
| Saccharin | 0.020 | 0.011 |
| Aspartame | 0.005 | 0.015 |
| Fenchyl ester | 0.0005 | 0.0036 |
| $CO_2$ | 3.5 (volumes) | 3.5 (volumes) |

B. Toothpaste

The following toothpaste formulation is within the scope of the present invention:

| Ingredients | Wt. % |
|---|---|
| Calcium pyrophosphate | 40.00 |
| Sorbitol (70% aqueous solution) | 20.40 |
| Glycerine | 10.20 |
| Sodium coconut monoglyceride sulfonate | 0.80 |
| Sodium carboxymethyl cellulose | 1.20 |
| Sodium coconut alkyl sulfate (20% active) | 2.30 |
| Sodium fluoride | 0.22 |
| Sweetener (Example 7) | 0.016 |
| Flavor | 0.90 |
| Red urea formaldehyde agglomerates | 0.65 |
| Water and minor ingredients | Balance |

C. Mouthwash

A mouthwash according to the present invention is prepared by co-dissolving the following ingredients:

| Ingredient | Percent by Weight |
|---|---|
| Glycerine | 10.00 |
| Ethyl alcohol | 17.00 |
| Cetyl pyridinium chloride | 0.05 |
| Sorbitan monooleate polyoxyethylene | 0.13 |
| Flavor (Oil of Wintergreen) | 0.09 |
| Sweetening agent* | 0.02 |
| Water and minor ingredients | Balance |

*Sweetener of Example 7, Hydrochloride salt

D. Dentifrice

A gel dentifrice having the following formulation is prepared by conventional means:

| Ingredients | Percent by Weight |
|---|---|
| Silica xerogel | 12.00 |
| Silica aerogel | 5.00 |
| Hydroxyethyl cellulose | 1.50 |
| Glycerine | 34.76 |
| Stannous fluoride | 0.41 |
| Flavor (Wintergreen) | 0.95 |
| Color (FD&C Blue #1) | 0.03 |
| 21% sodium lauryl sulfate-79% glycerine mixture | 6.00 |
| Sweetener* | 0.012 |
| Water and minor ingredients | Balance |

*Example 7, Calcium salt.

The above composition is prepared by blending and deaerating the listed ingredients in standard fashion.

E. Chewing Gum

A chewing gum is prepared by replacing the sucrose normally added to chewing gum with the sweeteners of the present invention. A gum base is prepared from:

| Ingredients | Weight in Grams |
|---|---|
| 60% latex | 18 |
| Hydrogenated rosin esters | 44 |
| Paracumarine resin | 7.5 |
| Candellila wax | 6 |
| Glyceryl tristearate | 2.5 |
| Ethyl cellulose | 2 |
| Calcium carbonate | 20 |

The gum base is used with the sweeteners of the present invention to prepare a chewing gum having a greatly reduced sugar content.

| Ingredients | Percent by Weight |
|---|---|
| Gum base | 68 |
| Sweetener* | 0.6 |
| Corn syrup | 16 |
| Flavor | 1 |

*Example 7

Chewing gum can also be prepared using other sweeteners of the present invention.

F. Powdered Sweeteners Concentrate

| | |
|---|---|
| Sweetener of Example 7, Hydrochloride Salt | 6.4 mg. |
| Dextrose | 840 mg. |

One packet containing the foregoing ingredients will be the approximate equivalent of two teaspoons of sugar.

H. Liquid Sweetener Concentrate

| | Gm. % |
|---|---|
| Example 7, Hydrochloride | 0.12 |
| Benzoic acid | 0.1 |
| Methyl paraben | 0.05 |
| Water | Balance |

Ten drops provides the approximate sweetening power of one teaspoon of sugar.

Specific Embodiments of Oral Products Containing Alpha-L-Aspartyl-D-Furylglycine and Alpha-L-Aspartyl-D-Thienylglycine Esters and Amides

A Carbonated Beverage

An orange flavored beverage syrup using the sweetener of Example 16 (50:50 mixture of D-furyl:L-furyl isomers) was made by mixing together the following ingredients:

| Ingredient | Amount (g.) |
|---|---|
| Water | 110 |
| Sodium benzoate | 0.38 |
| Granulated sugar | 52.18 |
| Citric acid | 1.17 |
| Sweetener of Example 16 | 0.0065 |
| Emulsified orange flavor concentrate | 2.48 |
| Ascorbic acid | 0.62 |

The above beverage syrup (28.2 g) was mixed with water up to 71.8 ml, and then with carbonated water (5.4 volumes $CO_2$) to provide 125 ml of a carbonated orange flavored beverage.

B Chocolate Milk

A chocolate flavored milk using the sweetener of Example 16 (50:50 mixture of D-furyl:L-furyl isomers) was made from the following ingredients:

| Ingredient | Amount (g.) |
| --- | --- |
| Hershey's cocoa | 2.5 |
| Sugar | 5 |
| Milk | 113 (ml) |
| Sweetener of Example 16 | 0.0006 |

The chocolate milk was made by adding a small portion of the total milk to the dry ingredients (sugar, cocoa, sweetener), mixing these ingredients together to form a smooth paste and then slowly adding the remainder of the milk with stirring.

C. Chocolate Pudding

A chocolate flavored pudding using the sweetener of Example 16 (50:50 mixture of D-furyl:L-furyl isomers) was made from the following ingredients:

| Ingredient | Amount (g.) |
| --- | --- |
| Sugar | 25 |
| Cornstarch | 3.5 |
| Hershey's cocoa | 7.0 |
| Milk | 110 |
| Margarine | 7.5 |
| Vanilla extract (35% alcohol) | 1 |
| Polydextrose* | 25 |
| Sweetener of Example 16 | 0.0031 |
| Salt | 0.3 |

*modified polydextrose made and sold by Pfizer, Inc.

The sugar, polydextrose, cornstarch, cocoa and salt were blended together first. The milk was then slowly added to the blended ingredients with stirring. This milk-containing mixture was brought to a boil over medium heat with occasional stirring, and then cooked for two additional minutes with stirring. The cooked mixture was removed from the heat and then the margarine, vanilla extract and sweetener were blended in. This blended mixture was chilled to form the chocolate pudding.

D. Cookies

Cookies were made using the sweetener of Example 16 (50:50 mixture of D-furyl:L:furyl isomers) as follows: The following ingredients were mixed together:

| Ingredient | Amount (g) |
| --- | --- |
| Margarine | 14 |
| Crisco shortening | 12.5 |
| Light brown sugar | 19.68 |
| Amaizo Lo-Dex ® 15 malto-dextrin | 19.68 |
| Sweetener of Example 16 | 0.0025 |

The mixed ingredients were creamed and then 0.5 g of vanilla extract (35% alcohol) and 12.0 g of beaten whole fresh eggs were added. This mixture was blended together and then flour (35.25 g), baking soda (0.5 g) and salt (0.625 g) were added. This mixture was blended together to form a cookie dough. This cookie dough was formed into dough pieces which were baked at 375° F. for 8.5 min. to provide cookies.

E. Toothpaste

The following toothpaste formulation is within the scope of the present invention:

| Ingredient | Wt. % |
| --- | --- |
| Calcium pyrophosphate | 40.00 |
| Sorbitol (70% aqueous solution) | 20.40 |
| Glycerine | 10.20 |
| Sodium coconut monoglyceride sulfonate | 0.80 |
| Sodium carboxymethyl cellulose | 1.20 |
| Sodium coconut alkyl sulfate (20% active) | 2.30 |
| Sodium fluoride | 0.22 |
| Sweetener (Example 20) | 0.014 |
| Flavor | 0.90 |
| Red urea formaldehyde agglomerates | 0.65 |
| Water and minor ingredients | Balance |

F. Mouthwash

A mouthwash according to the present invention is prepared by co-dissolving the following ingredients:

| Ingredient | Percent by Weight |
| --- | --- |
| Glycerine | 10.00 |
| Ethyl alcohol | 17.00 |
| Cetyl pyridinium chloride | 0.05 |
| Sorbitan monooleate polyoxyethylene | 0.13 |
| Flavor (Oil of Wintergreen) | 0.09 |
| Sweetening agent* | 0.017 |
| Water and minor ingredients | Balance |

*Sweetener of Example 19, Hydrochloride salt

G. Dentifrice

A gel dentifrice having the following formulation is prepared by conventional means:

| Ingredient | Percent by Weight |
| --- | --- |
| Silica xerogel | 12.00 |
| Silica aerogel | 5.00 |
| Hydroxyethyl cellulose | 1.50 |
| Glycerine | 34.76 |
| Stannous fluoride | 0.41 |
| Flavor (Wintergreen) | 0.95 |
| Color (FD&C Blue #1) | 0.03 |
| 21% sodium lauryl sulfate-79% glycerine mixture | 6.00 |
| Sweetener* | 0.042 |
| Water and minor ingredients | Balance |

*Example 17, Calcium salt.

The above composition is prepared by blending and deaerating the listed ingredients in standard fashion.

H. Chewing Gum

A chewing gum is prepared by replacing the sucrose normally added to chewing gum with the sweeteners of the present invention. A gum base is prepared from:

| Ingredients | Weight in Grams |
| --- | --- |
| 60% latex | 18 |
| Hydrogenated rosin esters | 44 |
| Paracumarine resin | 7.5 |
| Candellila wax | 6 |
| Glyceryl tristearate | 2.5 |
| Ethyl cellulose | 2 |
| Calcium carbonate | 20 |

The gum base is used with the sweeteners of the present invention to prepare a chewing gum having a greatly reduced sugar content.

| Ingredient | Percent by Weight |
|---|---|
| Gum base | 83 |
| Sweetener* | 0.0028 |
| Corn syrup | 16 |
| Flavor | 1 |

*Example 1b

Chewing gum can also be prepared using other sweeteners of the present invention.

I. Powdered Sweetener Concentrate

| Sweetener of Example 20, Hydrochloride Salt | 22.4 mg. |
|---|---|
| Dextrose | 840 mg. |

One packet containing the foregoing ingredients will be the approximate equivalent of two teaspoons of sugar.

J. Liquid Sweetener Concentrate

| | Gm. % |
|---|---|
| Example 20, Hydrochloride | 0.42 |
| Benzoic acid | 0.1 |
| Methyl paraben | 0.05 |
| Water | Balance |

Ten drops provides the approximate sweetening power of one teaspoon of sugar.

What is claimed is:

1. A compound of formula:

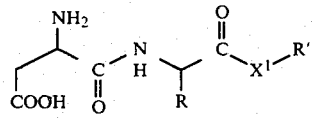

wherein the said ester or amide is the L, D stereochemical isomer; wherein $X^1$ is O or NH; and wherein R is a phenyl group having the formula:

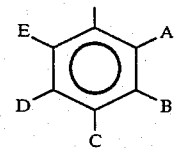

wherein, A, B, C, D and E are H, OH, F, Cl, Br, or $C_1$-$C_4$ alkyl, hydroxyalkyl or alkoxy; and wherein R' is selected from the group consisting of hydrocarbyl radicals having formulas (a) (b) (c) (d) (e) (f) and (g):

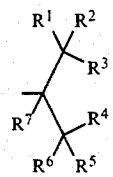 (a)

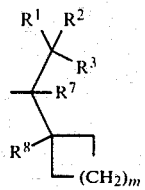 (b)

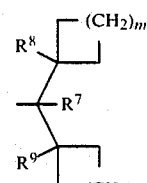 (c)

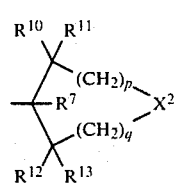 (d)

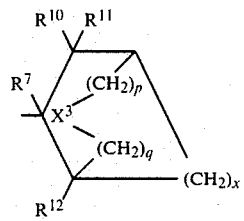 (e)

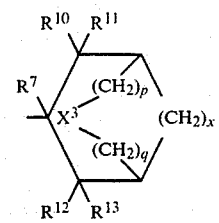 (f)

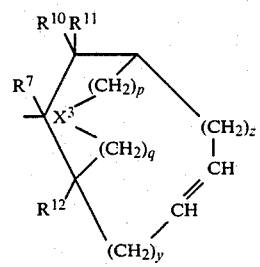 (g)

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are H, or $C_1$-$C_4$ alkyl, hydroxyalkyl or alkoxy; $X^2$ is $CH_2$, O, S, SO, $SO_2$, C=O, $CR^{14}OH$, $NR^{14}$

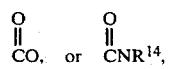

wherein $R^{14}$ is H or $C_1$-$C_2$ alkyl or hydroxyalkyl; $X^3$ is $CH_2$, O, S, SO, $SO_2$, C=O, $CR^{14}OH$, $NR^{14}$,

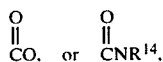

provided that when $X^3$ is other than $CH_2$, $R^{10}$, $R^{11}$, $R^{12}$ and $R^{13}$ are each H; m is 0, 1, 2, 3, or 4; n is 0, 1, 2, 3, or 4; p and q are 0. 1, 2 or 3 and the sum of p+q is not greater than 3; x is 1, 2 or 3; y and z are 0, 1 or 2 and the sum of y+z is not greater than 2; and nontoxic salts thereof.

2. The compound of claim 1 wherein one of A, B, C, D and E are OH or F, the remainder being H.

3. The compound of claim 2 wherein C is OH, and A, B, D and E are each H.

4. The compound of claim 1 wherein A, B, C, D and E are each H.

5. The compound of claim 4 wherein R' has the formula (a):

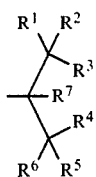

6. The compound of claim 5 wherein $R^1$, $R^2$, $R^3$, $R^4$, $R^5$, $R^6$, and $R^7$ are selected from methyl or hydrogen.

7. The compound of claim 6 wherein R' is diisopropylcarbinyl, or 3,3-dimethyl-2-butyl.

8. The compound of claim 4 wherein R' has the formula (b):

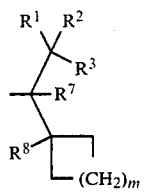

9. The compound of claim 8 wherein R' is tert-butyl cyclopropylcarbinyl.

10. The compound of claim 4 wherein R' has the formula (c):

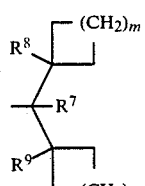

11. The compound of claim 10 wherein R' is dicyclopropylcarbinyl.

12. The compound of claim 4 wherein R' has the formula (d):

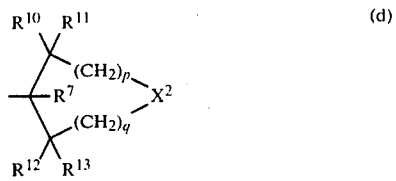

13. The compound of claim 12 wherein $X^2$ is $CH_2$, S, SO or $SO_2$.

14. The compound of claim 13 wherein R' is 2-methylcyclohexyl; 2-ethylcyclohexyl; 2-isopropylcyclohexyl; 2-tert-butyl cyclohexyl; 2,2-dimethylcyclohexyl; 2,6-dimethylcyclohexyl; 2,6-diethylcyclohexyl; 2,2,6-trimethylcyclohexyl; 2,2,6,6-tetramethylcyclohexyl; 2-isopropylcyclopentyl; 2-methylcyclopentyl; 2-ethylcyclopentyl; 2,2-dimethylcyclopentyl; 2,5-dimethylcyclopentyl; 2,2,5-trimethylcyclopentyl; 2,2,5,5-tetramethylcyclopentyl; 2,2,4,4-tetramethylthietan-3-yl; 2,2,4,4-tetramethyl-1-oxothietan-3-yl; 2,2,4,4-tetramethyl-1,1-dioxothietan-3-yl; or 2,2,4,4-tetramethyltetrahydrothiophene-3-yl.

15. The compound of claim 14 wherein R' is 2,5-dimethylcyclopentyl; 2,6-dimethylcyclohexyl; 2,2,5,5-tetramethylcyclopentyl; or 2,2,4,4-tetramethylthientan-3-yl.

16. The compound of claim 4 wherein R' has the formula (e):

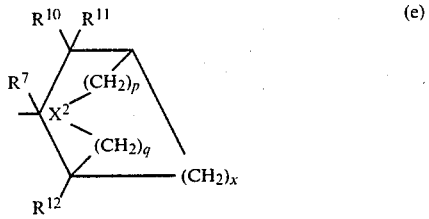

17. The compound of claim 16 wherein $X^1$ is O and R' is (±)-endo-norbonyl; (±)-exo-norbonyl; (±)-alpha-fenchyl; or (±)-beta-fenchyl.

18. The compound of claim 17 wherein R' is (−)-alpha-fenchyl; or (+)-beta-fenchyl.

19. A diastereomeric mixture of the compound of claim 1 wherein the L, D stereochemical isomer comprises at least about 50% of the mixture.

20. The diastereomeric mixture of claim 19 wherein the L, D stereochemical isomer comprises at least about 70% of the mixture.

21. The diastereomeric mixture of claim 20 wherein the L, D stereochemical isomer comprises at least about 95% of the mixture.

22. A mixture of the compound of claim 1 with a sweetener selected from the group consisting of saccharin and alpha-L-aspartyl-L-phenylalanine methyl ester in a ratio of from about 2:1 to about 1:9 on a sweetness equivalent basis.

* * * * *